(12) United States Patent (10) Patent No.: US 7,863,323 B1
Williams et al. (45) Date of Patent: Jan. 4, 2011

(54) FLAVONOLS

(75) Inventors: Spencer J. Williams, Kensington (AU);
Owen L. Woodman, Coburg (AU);
SuWan Yap, North Melbourne (AU)

(73) Assignee: The University of Melbourne, Victoria (AU)

(*) Notice: Subject to any disclaimer, the term of this patent is extended or adjusted under 35 U.S.C. 154(b) by 943 days.

(21) Appl. No.: 11/588,795

(22) Filed: Oct. 27, 2006

(51) Int. Cl.
*A61K 31/352* (2006.01)
*C07D 311/30* (2006.01)

(52) U.S. Cl. ........................ 514/456; 549/400
(58) Field of Classification Search .......... 549/400; 514/456
See application file for complete search history.

(56) References Cited

U.S. PATENT DOCUMENTS 6,329,189 B1* 12/2001 Kinoshita et al. ............ 435/232
2005/0245487 A1 11/2005 Murphy et al.

OTHER PUBLICATIONS

Picq et al, J. Med. Chem., vol. 25, pp. 1192-1198 (1982).*
Valenti et al, Anti-Cancer Drug Desigh vol. 11, p. 243-252 (1996).*
Adlam, et al., "Targeting an antioxidant to mitochondria decreases cardiac ischemia-reperfusion injury" in *The FASEB Journal*, Research Communication, (Jul. 2005), vol. 19, pp. 1088-1095.
Van Acker, et al., "Synthesis of Novel 3.7-Substituted-2-(3',4'-dihydroxyphenyl) flavones with Improved Antioxidant Activity" *J. Med. Chem*, (2000), vol. 43, pp. 3752-3760.
Woodman, et al., "Vascular and Anti-Oxidant Actions of Flavonols and Flavones" *Clinical and Experimental Pharmacology and Physiology*, (2004), vol. 31, pp. 786-790.
Calias, et al., "Synthesis of inositol 2-phosphate-quercetin conjugates" *Carbohydrate Research*, (1996), vol. 292, pp. 83-90.

* cited by examiner

*Primary Examiner*—Bernard Dentz
(74) *Attorney, Agent, or Firm*—Dunlap Codding, P.C.

(57) ABSTRACT

A compound of the formula (I):

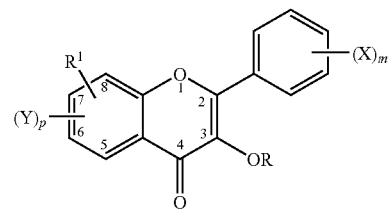

wherein
R is selected from the group consisting of H, alkyl, alkenyl, alkynyl, heteroalkyl, cycloalkyl, heterocycloalkyl, aryl, heteroaryl and acyl, each of which may be optionally substituted;
$R^1$ is an organic moiety that is capable of being converted into a charged group;
each X and Y is independently selected from the group consisting of H, halogen, —CN, —$NO_2$, —$CF_3$, —$OCF_3$, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, arylheteroalkyl, heterocycloalkylheteroalkyl, heteroarylheteroalkyl, hydroxy, hydroxyalkyl, alkoxy, alkoxyalkyl, alkoxyaryl, alkenyloxy, alkynyloxy, cycloalkyloxy, heterocycloalkyloxy, aryloxy, heteroaryloxy, arylalkyloxy, phenoxy, benzyloxy, amino, alkylamino, aminoalkyl, acylamino, arylamino, sulfonylamino, sulfinylamino, —COOH, —$COR^2$, —$COOR^2$, —$CONHR^2$, —$NHCOR^2$, —$NHCOOR^2$, —$NHCONHR^2$, $C(=NOH)R^2$, alkoxycarbonyl, alkylaminocarbonyl, sulfonyl, alkylsulfonyl, alkylsulfinyl, arylsulfonyl, arylsulfinyl, aminosulfonyl, $SR^2$ and acyl, each of which may be optionally substituted;
each $R^2$ is independently selected from the group consisting of H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl, and acyl, each of which may be optionally substituted;
m is an integer selected from the group consisting of 0, 1, 2, 3, 4 and 5;
p is an integer selected from 0, 1, 2 and 3;
or a pharmaceutically acceptable salt or prodrug thereof.

10 Claims, No Drawings

FLAVONOLS

CROSS-REFERENCE TO RELATED APPLICATIONS

Not applicable.

STATEMENT REGARDING FEDERALLY SPONSORED RESEARCH OR DEVELOPMENT

Not applicable.

FIELD OF THE INVENTION

The present invention relates generally to flavonol compounds with improved properties that may be useful in the treatment of conditions that require an anti-oxidant effect such as cardiovascular disease, compositions containing the compounds, methods of treatment of such conditions using the compounds, and the use of these compounds in the preparation of medicaments for the treatment of conditions of this type. In another embodiment the invention relates to a method of reducing the vasodilatory effect of a flavonol compound whilst substantially maintaining or enhancing its anti-oxidant activity.

BACKGROUND OF THE INVENTION

There are a large number of conditions in which anti-oxidant activity has been implicated as being useful in the development of treatment regimes. These include acute conditions such as myocardial ischaemia, stroke, cardiac surgery (e.g. coronary bypass surgery), and chronic conditions such as diabetes, atherosclerosis and hypertension. Notwithstanding the prevalence of disorders of this type there is still the need to develop new drugs that can be used in the treatment of these conditions.

For example one of the best known of the conditions of this type, cardiovascular disease (CVD), is currently the leading cause of mortality worldwide in adults aged 60 years and above. While there are various types of CVD, the two most common causes of fatality are coronary heart disease and stroke. In 2002, the total number of deaths from CVD globally amounted to 16.7 million, of which approximately 7 million resulted from coronary heart disease and a further 6 million from stroke. In Australia, CVD is also the leading cause of death where 38% of all deaths in 2002 were a result of CVD. In addition, CVD causes long-term disability in 1.10 million Australians. Consequently, CVD represents a heavy economic burden with the direct costs of the disease estimated to be approximately $5.4 billion in 2000-1 in Australia, and $286 billion in 1999 in the United States of America, and it is predicted that this figure will continue to rise due to the aging population. Although CVD has long been thought to be a disease predominantly occurring in developed countries, it has become increasingly clear that it is also emerging in third-world countries and is already the leading cause of mortality in some regions of the developing world. As such, there is an urgent need to develop novel agents for the treatment or prevention of CVD.

The underlying cause of CVD is atherosclerosis, which is the development of fatty deposits on normally-smooth blood vessels, which start to form in people from a very young age. There are a number of risk factors such as obesity, high blood cholesterol and high blood pressure that predispose individuals to the formation of these fatty deposits, which in turn places them in a high risk category for CVD. As the fatty deposits continue to develop, the vessel narrows and the wall thickens, hardens and loses elasticity. Blood flow through these vessels is disturbed resulting in platelet activation, causing the formation of a thrombus at the site of the lesion, which occludes the vessel. When this occurs in the heart or brain, ischaemic heart disease or stroke, respectively, result.

Oxygen supply may be restored after ischaemic injury, by dislodging or dissolving the thrombus. However, paradoxically, restoration of the oxygen supply can lead to a worsened secondary condition known as reperfusion injury. The reintroduction of oxygen causes the production of reactive oxygen species (ROS), which exacerbates and accelerates the injury already produced by the ischaemia. ROS include free radicals that have an unpaired electron, such as $O_2^{.-}$ and $HO^{.}$, as well as other reactive species such as $H_2O_2$. $HO^{.}$ is particularly reactive and reacts indiscriminately with membrane lipids, proteins and DNA, degrading them and causing cellular damage. There are various sources of ROS, including nitric oxide synthase, myeloperoxidase, superoxide dismutase, mitochondrial electron transport, metabolism of arachidonic acid by cyclooxygenase and xanthine oxidase. One of the pathways for production of ROS is shown below.

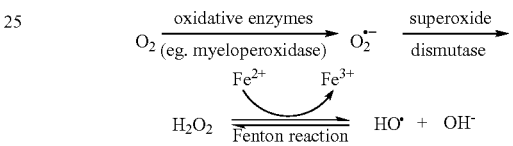

A diet high in cholesterol has long been known to be associated with CVD. Epidemiological studies have indicated that the French population has a lower than predicted incidence of CVD given their comparatively high fat diet. This anomaly is known as "The French Paradox" (9-11). With other risk factors for CVD, such as smoking and obesity, comparable to other Western populations, it has been suggested that the regular consumption of red wine in the French diet holds the key to cardio-protection. Later studies have suggested that it is a non-alcoholic component of wine, the flavonoids, that contribute to protective effects in the cardiovascular system. In other studies, flavonoids have been found to possess many beneficial properties, such as anti-inflammatory, anti-allergic, anti-viral, anti-thrombotic and anti-carcinogenic effects.

Flavonoids are polyphenolic compounds with many subclasses, and previous studies have shown a group of compounds called flavonols to be of particular interest for treatment of and protection against CVD. Flavonols possess 3 rings, with a hydroxyl group in the 3-position of the C ring. They are found in a large variety of plant materials, such as fruits, vegetables, nuts, seeds, herbs, spices, stems, flowers, tea and red wine, and have been consumed by humans since prehistoric times, suggesting that they are unlikely to possess significant adverse effects. Some structure-activity relationship studies have been performed to identify substituents on the flavonol ring system that are important for vasorelaxant and antioxidant activity. It has been found that the 3-OH group of the C ring was essential for endothelium-dependent vasorelaxant activity and additional hydroxyl groups at the 3' and 4' positions of the B ring further improves biological activity. For antioxidant activity, the 3-OH of the C ring, attached to the C2-C3 double bond, which is in conjugation with the 4-oxo group of the C ring, together with either a 4'-hydroxy or a 3',4'-catechol moiety on the B ring were shown to be important. Thus, the most potent flavonol for antioxidant and vasorelaxant activities described to date is 3',4'-dihydroxyflavonol (diOHF).

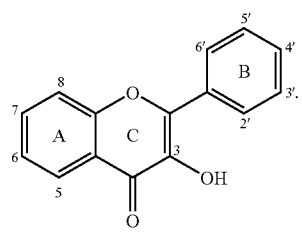

General structure of flavonols

There is significant potential for flavonols or flavonol analogues to be useful in the treatment of conditions which can be treated by anti-oxidants due to the strong anti-oxidant activity demonstrated by compounds of this general structural type. Unfortunately, however, there are a number of problems encountered for compounds of this general structural type that lead to a reduction in their ability to be used in this way. For example one undesirable property of compounds of this type is that they are generally insoluble in water making their use as drugs impractical. In addition many of these compounds display multiple biological activities, which in many instances is undesirable and limits their broad spectrum use. For example many of the flavonols display both anti-oxidant and vasodilatory activity. This is generally undesirable as it is preferable to be able to administer a drug with a single activity in order to limit the possible adverse side effects. In relation to flavonols which have both anti-oxidant and vasodilatory activity there are a number of instances in which such dual activity is undesirable. If the anti-oxidant activity is the desired end result then vasodilatory activity may lead to adverse side effects such as hypotension (excessively low blood pressure), postural hypotension (dizziness and possible collapse when moving from lying to standing), tachycardia (an excessively high heart rate to try to compensate for the low blood pressure) and arrhythmias. As such the fact that flavonols have both properties is undesirable. It would therefore be desirable to develop flavonols with improved specificity as current flavonols do not possess any selectivity of note.

It would therefore be desirable to overcome or ameliorate one or more of the observed problems with the flavonol compounds as discussed above.

The present invention is based on the finding by the present applicants that modification of flavonols or flavonol compounds in certain pre-defined ways leads to improvements in the functional performance of the compounds and addresses one or more of the deficiencies identified above.

SUMMARY OF THE INVENTION

In a first aspect the present invention provides a compound of formula (I):

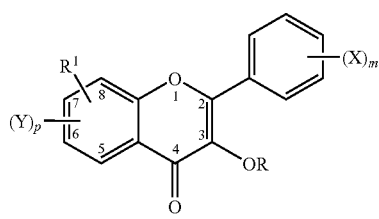

Formula (I)

wherein

R is selected from the group consisting of H, alkyl, alkenyl, alkynyl, heteroalkyl, cycloalkyl, heterocycloalkyl, aryl, heteroaryl and acyl, each of which may be optionally substituted;

$R^1$ is an organic moiety that is capable of being converted into a charged group;

each X and Y is independently selected from the group consisting of H, halogen, —CN, —NO$_2$, —CF$_3$, —OCF$_3$, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, arylheteroalkyl, heterocycloalkylheteroalkyl, heteroarylheteroalkyl, hydroxy, hydroxyalkyl, alkoxy, alkoxyalkyl, alkoxyaryl, alkenyloxy, alkynyloxy, cycloalkyloxy, heterocycloalkyloxy, aryloxy, heteroaryloxy, arylalkyloxy, phenoxy, benzyloxy, amino, alkylamino, aminoalkyl, acylamino, arylamino, sulfonylamino, sulfinylamino, —COOH, —COR$^2$, —COOR$^2$, —CONHR$^2$, —NHCOR$^2$, —NHCOOR$^2$, —NHCONHR$^2$, C(=NOH)R$^2$, alkoxycarbonyl, alkylaminocarbonyl, sulfonyl, alkylsulfonyl, alkylsulfinyl, arylsulfonyl, arylsulfinyl, aminosulfonyl, SR$^2$ and acyl, each of which may be optionally substituted;

each $R^2$ is independently selected from the group consisting of H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl, and acyl, each of which may be optionally substituted;

m is an integer selected from the group consisting of 0, 1, 2, 3, 4 and 5;

p is an integer selected from the group consisting of 0, 1, 2 and 3;

or a pharmaceutically acceptable salt or prodrug thereof.

In one embodiment of the compounds of the invention R is H.

In one embodiment of the compounds of the invention m is selected from the group consisting of 0, 1 and 2.

In one embodiment of the compounds of the invention X is OH.

In one embodiment of the invention $R^1$ is an ionisable group. In one form of this embodiment $R^1$ is selected from the group consisting of:

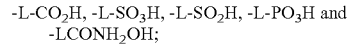

wherein L is a linking moiety containing from 1 to 20 atoms in the normal chain, more preferably from 1 to 10 atoms in the normal chain, most preferably from 1 to 4 atoms in the normal chain.

In one embodiment $R^1$ is a group of formula -L-CO$_2$H. In one specific embodiment $R^1$ is a group of formula —NHCO(CH$_2$)$_2$CO$_2$H. In another specific embodiment R1 is a group of the formula —OCH$_2$CO$_2$H.

In one embodiment of the compounds of the invention Y=H and p=3.

Specific examples of compounds of the invention are selected from the group consisting of:

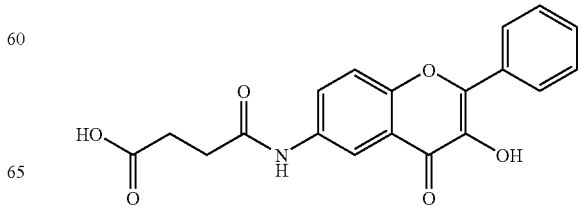

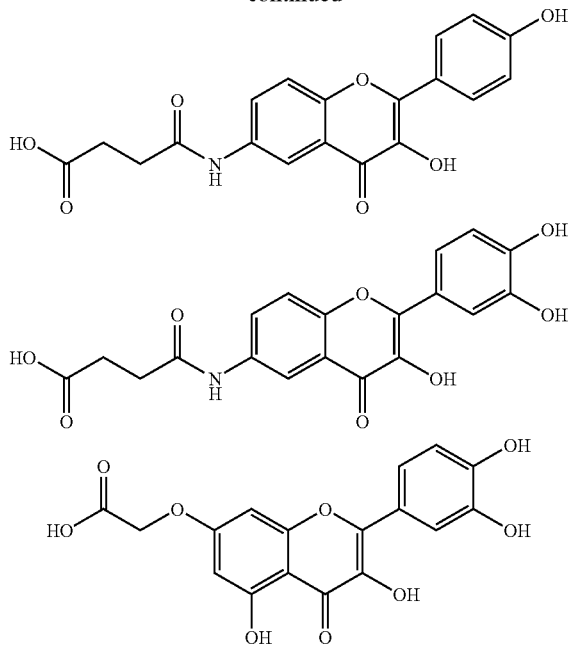

In a further aspect the invention provides pharmaceutical compositions including a compound of the invention as described above and a pharmaceutically acceptable carrier, diluent or excipient.

In an even further aspect the invention provides a method of treatment of a condition that may be treated by administration of an anti-oxidant, the method including administration of a therapeutically effective amount of a compound of the invention.

In an even further aspect the invention provides the use of a compound of the invention in the preparation of a medicament for the treatment or prophylaxis of a condition that can be treated by administration of an anti-oxidant.

In an even further aspect the invention provides a method of reducing the vasodilatory activity of a compound of the formula (II) whilst substantially conserving or enhancing the antioxidant activity of the compound, the method including the step of converting the compound of formula (II)

Formula (II)

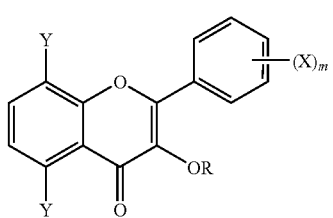

wherein

R is selected from the group consisting of H, alkyl, alkenyl, alkynyl, heteroalkyl, cycloalkyl, heterocycloalkyl, aryl, heteroaryl and acyl, each of which may be optionally substituted;

each X and Y is independently selected from the group consisting of H, halogen, —CN, —NO$_2$, —CF$_3$, —OCF$_3$, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, arylheteroalkyl, heterocycloalkylheteroalkyl, heteroarylheteroalkyl, hydroxy, hydroxyalkyl, alkoxy, alkoxyalkyl, alkoxyaryl, alkenyloxy, alkynyloxy, cycloalkyloxy, heterocycloalkyloxy, aryloxy, heteroaryloxy, arylalkyloxy, phenoxy, benzyloxy, amino, alkylamino, aminoalkyl, acylamino, arylamino, sulfonylamino, sulfinylamino, —COOH, —COR$^2$, —COOR$^2$, —CONHR$^2$, —NHCOR$^2$, —NHCOOR$^2$, —NHCONHR$^2$, C(=NOH)R$^2$, alkoxycarbonyl, alkylaminocarbonyl, sulfonyl, alkylsulfonyl, alkylsulfinyl, arylsulfonyl, arylsulfinyl, aminosulfonyl, SR$^2$ and acyl, each of which may be optionally substituted;

each R$^2$ is independently selected from the group consisting of H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl, and acyl, each of which may be optionally substituted;

m is an integer selected from the group consisting of 0, 1, 2, 3, 4 and 5;

or a pharmaceutically acceptable salt or prodrug thereof into a compound of formula (III)

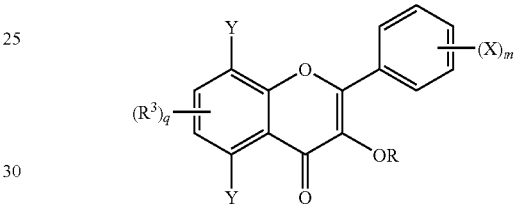

wherein R$^3$ is selected from the group consisting of halogen, —CN, —NO$_2$, —CF$_3$, —OCF$_3$, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, arylheteroalkyl, heterocycloalkylheteroalkyl, heteroarylheteroalkyl, hydroxy, hydroxyalkyl, alkoxy, alkoxyalkyl, alkoxyaryl, alkenyloxy, alkynyloxy, cycloalkyloxy, heterocycloalkyloxy, aryloxy, heteroaryloxy, arylalkyloxy, phenoxy, benzyloxy, amino, alkylamino, aminoalkyl, acylamino, arylamino, sulfonylamino, sulfinylamino, —COOH, —COR$^2$, —COOR$^2$, —CONHR$^2$, —NHCOR$^2$, —NHCOOR$^2$, —NHCONHR$^2$, C(=NOH)R$^2$, alkoxycarbonyl, alkylaminocarbonyl, sulfonyl, alkylsulfonyl, alkylsulfinyl, arylsulfonyl, arylsulfinyl, aminosulfonyl, SR$^2$ and acyl, each of which may be optionally substituted, or R$^3$ is an organic moiety capable of being converted into a charged group;

and q is 1 or 2.

In one embodiment of the method the compound of formula (II) is converted into a compound of formula (IIIa)

Formula (IIIa)

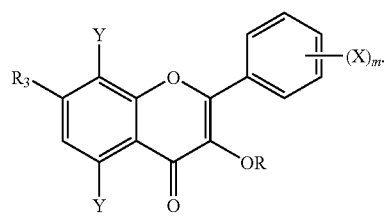

In another embodiment of the method the compound of formula (II) is converted into a compound of formula (IIIb)

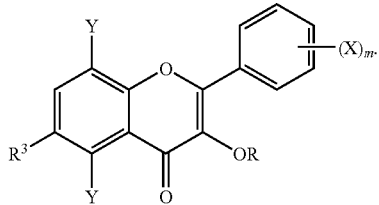

Formula (IIIb)

In another embodiment of the method the compound is converted into a compound of formula (IIIc)

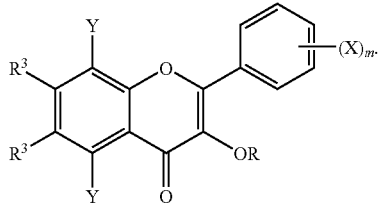

Formula (IIIc)

In one embodiment of the method of the invention R is H.

In one embodiment of the methods of the invention m is selected from the group consisting of 0, 1 and 2.

In one embodiment of the methods of the invention X is OH.

In one embodiment of the methods of the invention Y is H or OH.

In one embodiment of the method $R^3$ is an ionisable group. In a further embodiment $R^3$ is selected from the group consisting of:

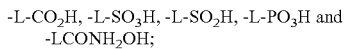

wherein L is a linking moiety containing from 1 to 20 atoms in the normal chain, more preferably from 1 to 10 atoms in the normal chain, most preferably from 1 to 4 atoms in the normal chain. In one embodiment of the method $R^3$ is a group of formula -L-$CO_2$H. In another specific embodiment $R^3$ is a group of formula —NHCO($CH_2$)$_2$$CO_2$H. In another specific embodiment $R^1$ is a group of the formula —O$CH_2$$CO_2$H.

In yet an even further aspect the invention includes a method of achieving an anti-oxidant effect in a subject without eliciting a vasodilatory effect in the subject, the method including administering an effective amount of a compound of the invention to the subject:

DETAILED DESCRIPTION OF THE INVENTION

In this specification a number of terms are used which are well known to a skilled addressee. Nevertheless for the purposes of clarity a number of terms will be defined.

As used herein, the term unsubstituted means that there is no substituent or that the only substituents are hydrogen.

The term "optionally substituted" as used throughout the specification denotes that the group may or may not be further substituted or fused (so as to form a condensed polycyclic system), with one or more substituent groups. Preferably the substituent groups are one or more groups independently selected from the group consisting of halogen, =O, =S, —CN, —$NO_2$, —$CF_3$, —$OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, arylheteroalkyl, heteroarylheteroalkyl, hydroxy, hydroxyalkyl, alkoxy, alkoxyalkyl, alkoxycycloalkyl, alkoxyheterocycloalkyl, alkoxyaryl, alkoxyheteroaryl, alkoxycarbonyl, alkylaminocarbonyl, alkenyloxy, alkynyloxy, cycloalkyloxy, cycloalkenyloxy, heterocycloalkyloxy, heterocycloalkenyloxy, aryloxy, phenoxy, benzyloxy, heteroaryloxy, arylalkyloxy, arylalkyl, heteroarylalkyl, cycloalkylalkyl, heterocycloalkylalkyl, arylalkyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, alkylsulfinyl, arylsulfinyl, aminosulfinylaminoalkyl, —COON, —$COR^2$, —C(O)$OR^2$, —CONH$R^2$, —NHCO$R^2$, —NHCOO$R^2$, NHCONH$R^2$, C(=NOH)$R^2$, —SH, —$SR^2$, —$OR^2$, acyl, a group of formula —N($R^2$)$_2$ or —CON($R^2$)$_2$ or a group of formula —NHCON($R^2$)$_2$.

"Alkyl" as a group or part of a group refers to a straight or branched aliphatic hydrocarbon group, preferably a $C_1$-$C_{14}$ alkyl, more preferably $C_1$-$C_{10}$ alkyl, most preferably $C_1$-$C_6$ unless otherwise noted. Examples of suitable straight and branched $C_1$-$C_6$ alkyl substituents include methyl, ethyl, n-propyl, 2-propyl, n-butyl, sec-butyl, t-butyl, hexyl, and the like. When alkyl is used as a bridging group it is typically (but not exclusively) referred to as alkylene. A similar convention applies to other bridging groups.

"Acyl" means an alkyl-CO— group in which the alkyl group is as described herein. Examples of acyl include acetyl and benzoyl. The alkyl group is preferably a $C_1$-$C_6$ alkyl group.

"Alkenyl" as a group or part of a group denotes an aliphatic hydrocarbon group containing at least one carbon-carbon double bond and which may be straight or branched preferably having 2-14 carbon atoms, more preferably 2-12 carbon atoms, most preferably 2-6 carbon atoms, in the normal chain. The group may contain a plurality of double bonds in the normal chain and the orientation about each is independently E or Z. Exemplary alkenyl groups include, but are not limited to, ethenyl, propenyl, butenyl, pentenyl, hexenyl, heptenyl, octenyl and nonenyl.

"Alkoxy" refers to an —O-alkyl group in which alkyl is defined herein. Preferably the alkoxy is a $C_1$-$C_6$alkoxy. Examples include, but are not limited to, methoxy and ethoxy.

"Alkynyl" as a group or part of a group means an aliphatic hydrocarbon group containing a carbon-carbon triple bond and which may be straight or branched preferably having from 2-14 carbon atoms, more preferably 2-12 carbon atoms, more preferably 2-6 carbon atoms in the normal chain. Exemplary structures include, but are not limited to, ethynyl and propynyl.

"Cycloalkyl" refers to a saturated or partially saturated, monocyclic or fused or spiro polycyclic, carbocycle preferably containing from 3 to 9 carbons per ring, such as cyclopropyl, cyclobutyl, cyclopentyl, cyclohexyl and the like, unless otherwise specified. It includes monocyclic systems such as cyclopropyl and cyclohexyl, bicyclic systems such as decalin, and polycyclic systems such as adamantane.

"Heterocycloalkyl" refers to a saturated or partially saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morpholino, 1,3-diazapane, 1,4-diazapane, 1,4-oxazepane, and 1,4-oxathiapane.

"Heteroalkyl" refers to a straight- or branched-chain alkyl group preferably having from 2 to 14 carbons, more preferably 2 to 10 atoms in the chain, one or more of which is a heteroatom selected from S, O, and N. Exemplary heteroalkyls include alkyl ethers, secondary and tertiary alkyl amines, alkyl sulfides, and the like.

"Aryl" as a group or part of a group denotes (i) an optionally substituted monocyclic, or fused polycyclic, aromatic carbocycle (ring structure having ring atoms that are all carbon) preferably having from 5 to 12 atoms per ring. Examples of aryl groups include phenyl, naphthyl, and the like; (ii) an optionally substituted partially saturated bicyclic aromatic carbocyclic moiety in which a phenyl and a $C_{5-7}$ cycloalkyl or $C_{5-7}$ cycloalkenyl group are fused together to form a cyclic structure, such as tetrahydronaphthyl, indenyl or indanyl.

"Heteroaryl" either alone or part of a group refers to groups containing an aromatic ring (preferably a 5 or 6 membered aromatic ring) having one or more heteroatoms as ring atoms in the aromatic ring with the remainder of the ring atoms being carbon atoms. Suitable heteroatoms include nitrogen, oxygen and sulphur. Examples of heteroaryl include thiophene, benzothiophene, benzofuran, benzimidazole, benzoxazole, benzothiazole, benzisothiazole, naphtho[2,3-b]thiophene, furan, isoindolizine, xantholene, phenoxatine, pyrrole, imidazole, pyrazole, pyridine, pyrazine, pyrimidine, pyridazine, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, 2-,3- or 4-pyridyl, 2-, 3-, 4-, 5-, or 8-quinolyl, 1-, 3-, 4-, or 5-isoquinolinyl 1-, 2-, or 3-indolyl, and 2-, or 3-thienyl.

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state.

The Compounds of the Invention

The compounds of the invention were developed with a view to probing ways of increasing the water solubility (and hence bioavailability) of the flavonols or flavonol analogues. The approach was to identify chemical modifications to the general structural backbone that could be made that would lead to increased chemical solubility but that would not destroy the activity of the compounds.

Studies that have been carried out on structure activity relationships of flavonols and flavonol analogues suggest that the important portions of the molecule for anti-oxidant activity were the substitution pattern on the B and C rings. As such initial studies into the area were focussed on elaboration of the A ring or the A ring substituents. Whilst there are a vast number of chemical modifications that could be made there was some concern that if the elaboration was too extreme it would lead to a loss of activity. As such in making the desired modifications an attempt was made to make the modifications as simple as possible. As a model system for the flavonols and analogs thereof a simple member of this series was chosen along with its analogs namely compound A.

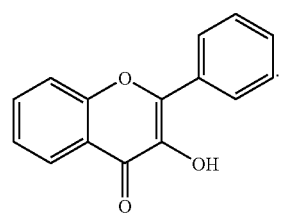

Compound A

It was also appreciated that the presence of reactive oxygen species (ROS) generated in mitochondria are believed to play a significant role in a number of common pathological states including diabetes and ischaemia-reperfusion injury.

The present inventors have found that the incorporation of an organic moiety containing a group capable of being converted into a charged group significantly increases the water solubility of the molecules of this type. There are a number of organic moieties that meet this criteria as would be well known in the art. There are a number of possible species that can be incorporated that are able to be converted into a charged species. A preferred example of such a species are basic nitrogen containing moieties.

In an alternative embodiment the group $R^1$ may be an ionisable group such that the group, under basic conditions, can be converted (ionised) into a negatively charged species. Alternatively, the group may be converted under acidic conditions into a positively charged species. Once again there are a number of possible moieties that would fit either of these descriptions with organic acids and the like being preferred examples of the first type and amine compounds being representative examples of the second.

A number of well known ionisable groups are well known in the art but it is preferred that $R^1$ is selected from the group consisting of:

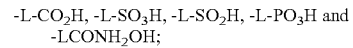
-L-CO$_2$H, -L-SO$_3$H, -L-SO$_2$H, -L-PO$_3$H and -LCONH$_2$OH;

wherein L is a linking moiety containing from 1 to 20 atoms in the normal chain. The length of the linking moiety may be varied but it preferably has from 1 to 10 atoms in the normal chain, more preferably from 1 to 4 atoms in the normal chain. The atoms in the chain may be only carbon atoms or the normal chain may also contain one or more heteroatoms.

It has been found that it is preferred that $R^1$ is a group of formula -L-CO$_2$H, most preferably a group of formula —NHCO(CH$_2$)$_2$CO$_2$H.

Following this general approach the following compounds were identified.

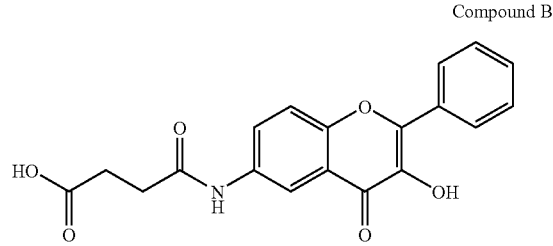

Compound B

-continued

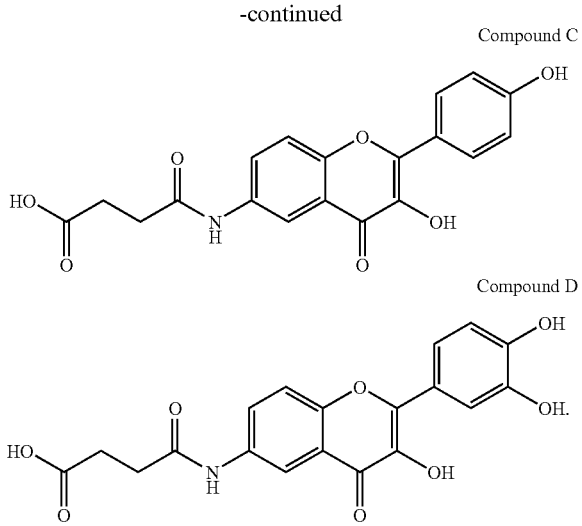

Compound C

Compound D

It was found that compounds B, C and D had improved solubility in comparison with the unmodified moiety. Whilst flavonols are water insoluble, it was found that the succinamic acid flavonols readily dissolved in 0.1 M $Na_2CO_3$ solution. The maximum concentrations attained were $10^{-1}$ M for compounds B and C and $10^{-2}$ M for compound D. The results demonstrate that the incorporation of a carboxylic acid moiety of this type can significantly improve the drug delivery properties of the flavonol type compounds.

Modulation of Vasodilatory Activity

The compounds synthesized were tested in order to determine their anti-oxidant and vasodilatory activity. These studies demonstrated that the modification proposed above whilst not having any significant effect on anti-oxidant activity lead to a reduction in vasodilatory activity.

Vasodilatory Activity

Vascular activity can be tested in standard organ bath assays using rat isolated thoracic aorta. The synthesized flavonols were first assayed for their ability to inhibit contractions induced by phenylephrine (PE), since it has been previously shown that flavonols can act as functional antagonists of PE. Next, the efficacy of the various flavonols would be determined in a direct relaxation assay. The vascular activities of the synthesized compounds were compared to diOHF since this is the most potent flavonol described to date. It was expected that the flavonols should reduce the magnitude of PE-induced contractions in endothelium-intact aortic rings, thus reducing the maximum response ($R_{max}$) for PE-induced contractions. FIG. 1 shows the results from these two assays.

As can be seen in FIG. 1a, the succinamic acid-substituted flavonols B, C and D were less effective than diOHF at inhibiting PE-induced contractions. In the case of D, which bears a catechol moiety like diOHF, vascular activity was completely abolished. This correlates with the results from the relaxation assay (FIG. 1b), where two of the synthesized compounds B and C showed weak vasorelaxation activity, and slight contractions were observed at high concentrations of D. The $pEC_{50}$ value for diOHF was found to be 5.33±0.07 (n=4) and $pEC_{50}$ values for the various flavonols were not determined as the data did not fit a sigmoidal curve. The maximum relaxation of the various flavonols is shown in Table 1, and are significantly different from each other (p<0.001).

Interestingly, compounds B and C, which possessed fewer hydroxyl groups on the B ring, exhibited some vascular activity, albeit less than diOHF, indicating that the introduction of the succinamic acid side chain does not always completely ablate vascular activity. While the mechanism by which flavonols exert their vascular activity remains controversial, there have been several suggestions as to its mode of activity, such as interference with second messenger proteins, protein kinase C and cAMP-phosphodiesterase, as well as inhibiting influx of extracellular calcium.

TABLE 1

Maximum response by the flavonols in the relaxation assay.

| Compound | n | $R_{max}$ (%) |
|---|---|---|
| B | 6 | 47 ± 2[a,b] |
| C | 4 | 80 ± 5[a,b] |
| D | 4 | −25 ± 3[a] |
| diOHF | 4 | 105 ± 2 |

[a]significant difference to diOHF;
[b]significant difference to D (p < 0.001, Newman-Keuls test).

Since the vascular activity of the synthesized flavonols was attenuated, it was of great interest to test these compounds for antioxidant activity. Antioxidant activity can be assessed in a tissue-based lucigenin-enhanced chemiluminescence assay. Isolated rat aortic rings were incubated with NADPH and the various flavonols. NADPH, a substrate for NADPH oxidase in the vasculature, increases superoxide production. Superoxide that is produced reacts with lucigenin, leading to the emission of photons, which can be quantified to give a measure of superoxide levels. If the flavonols possess antioxidant activity, superoxide levels will be reduced, resulting in a decrease in photon emission. Again, in this assay, the level of antioxidant activity of the various flavonols was compared with diOHF, one of the most potent flavonol antioxidants identified to date, and results are shown in FIG. 2.

As can be seen, compounds B and D possess moderate to good antioxidant activity whereas compound C had little effect. The activity of D is most promising, where superoxide levels were substantially reduced, approaching the activity of diOHF. This correlates with previous studies that have demonstrated that a catechol moiety on the B ring improves antioxidant activity. Thus, while modifications at the 6-position of the A ring showed vascular activity to be attenuated, antioxidant activity was shown to be largely retained especially in circumstances where there was a catechol moiety on the B ring.

As the results seem to indicate that there was the ability to retain the anti-oxidant activity of the flavonol whilst at the same time mediating the vasodilatory effect it has thus been shown that there is a mechanism by which a flavonol may be modified to both improve its solubility and to attenuate the vasodilatory activity without having a negative impact on the anti-oxidant activity.

The Therapeutic Approach

The compounds of the present invention can therefore be administered in any circumstance where it is desired to provide an anti-oxidant effect without a vasodilatory effect. As a general principle it is almost always desirable to administer a compound that has a single activity as it minimises the possibility of adverse side effects being encountered and at the same time allows the clinician to administer the desired dosage of the drug focussing solely on the desired outcome without having to be concerned by the possible negative implications of the treatment regimen. The present invention therefore provides the ability to achieve an anti-oxidant effect in a subject without eliciting a vasodilatory effect in the subject.

Administration of Compounds

Administration of compounds within Formula I to humans can be by any of the accepted modes of administration well known in the art. For example they may be administered by enteral administration such as oral or rectal, or by parenteral administration such as subcutaneous, intramuscular, intravenous and intradermal routes. Injection can be bolus or via constant or intermittent infusion. The active compound is typically included in a pharmaceutically acceptable carrier or diluent and in an amount sufficient to deliver to the subject a therapeutically effective dose.

It is anticipated that the compounds of the invention will be useful in treating a wide variety of disorders that are amenable to treatment with anti-oxidants. These include acute conditions such as myocardial ischaemia, stroke, cardiac surgery (e.g. coronary bypass surgery), and chronic conditions such as diabetes, atherosclerosis and hypertension.

In using the compounds of the invention they can be administered in any form or mode which makes the complex bioavailable. One skilled in the art of preparing formulations can readily select the proper form and mode of administration depending upon the particular characteristics of the compound selected, the condition to be treated, the stage of the condition to be treated and other relevant circumstances. We refer the reader to Remingtons Pharmaceutical Sciences, $19^{th}$ edition, Mack Publishing Co. (1995) for further information.

The compounds of the present invention can be administered alone or in the form of a pharmaceutical composition in combination with a pharmaceutically acceptable carrier, diluent or excipient.

The compounds are, however, typically used in the form of pharmaceutical compositions which are formulated depending on the desired mode of administration. As such, in a further embodiment the present invention provides a pharmaceutical composition including a compound of Formula (I) and a pharmaceutically acceptable carrier, diluent or excipient. The compositions are prepared in manners well known in the art.

The invention in other embodiments provides a pharmaceutical pack or kit comprising one or more containers filled with one or more of the ingredients of the pharmaceutical compositions of the invention. In such a pack or kit can be found a container having a unit dosage of the agent (s). The kits can include a composition comprising an effective agent either as concentrates (including lyophilized compositions), which can be diluted further prior to use or they can be provided at the concentration of use, where the vials may include one or more dosages. Conveniently, in the kits, single dosages can be provided in sterile vials so that the physician can employ the vials directly, where the vials will have the desired amount and concentration of agent(s). Associated with such container(s) can be various written materials such as instructions for use, or a notice in the form prescribed by a governmental agency regulating the manufacture, use or sale of pharmaceuticals or biological products, which notice reflects approval by the agency of manufacture, use or sale for human administration.

The compounds of the invention may be used or administered in combination with one or more additional drug (s) that are useful for the treatment of the disorder/diseases mentioned. The components can be administered in the same formulation or in separate formulations. If administered in separate formulations the compounds of the invention may be administered sequentially or simultaneously with the other drug(s).

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of micro-organisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminium monostearate and gelatin.

If desired, and for more effective distribution, the compounds can be incorporated into slow release or targeted delivery systems such as polymer matrices, liposomes, and microspheres.

The injectable formulations can be sterilized, for example, by filtration through a bacterial-retaining filter, or by incorporating sterilizing agents in the form of sterile solid compositions that can be dissolved or dispersed in sterile water or other sterile injectable medium just prior to use.

Solid dosage forms for oral administration include capsules, tablets, pills, powders, and granules. In such solid dosage forms, the active complex is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

If desired, and for more effective distribution, the compounds can be incorporated into slow release or targeted delivery systems such as polymer matrices, liposomes, and microspheres.

The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavouring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminium metahydroxide, bentonite, agar-agar, and tragacanth, and mixtures thereof.

Compositions for rectal or vaginal administration are preferably suppositories which can be prepared by mixing the complexes of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound of this invention include powders, patches, sprays, ointments and inhalants. The active compound is mixed under sterile conditions with a pharmaceutically acceptable carrier and any needed preservatives, buffers, or propellants which may be required.

The amount of compound administered will preferably treat and reduce or alleviate the condition. A therapeutically effective amount can be readily determined by an attending diagnostician by the use of conventional techniques and by observing results obtained under analogous circumstances. In determining the therapeutically effective amount a number of factors are to be considered including but not limited to, the species of animal, its size, age and general health, the specific condition involved, the severity of the condition, the response of the subject to treatment, the particular compound administered, the mode of administration, the bioavailability of the preparation administered, the dose regime selected, the use of other medications and other relevant circumstances.

A preferred dosage will be a range from about 0.01 to 300 mg per kilogram of body weight per day. A more preferred dosage will be in the range from 0.1 to 100 mg per kilogram of body weight per day, more preferably from 0.2 to 80 mg per kilogram of body weight per day, even more preferably 0.2 to 50 mg per kilogram of body weight per day. A suitable dose can be administered in multiple sub-doses per day.

Synthesis

The compounds of the various embodiments may be prepared using the reaction routes and synthesis schemes as described below, employing the techniques available in the art using starting materials that are readily available. The preparation of particular compounds of the embodiments is described in detail in the following examples, but the artisan will recognize that the chemical reactions described may be readily adapted to prepare a number of other agents of the various embodiments. For example, the synthesis of non-exemplified compounds may be successfully performed by modifications apparent to those skilled in the art, e.g. by appropriately protecting susceptible groups, by changing to other suitable reagents known in the art, or by making routine modifications of reaction conditions. A list of suitable protecting groups in organic synthesis can be found in Protective Groups in Organic Synthesis, T. W. Greene and P. G. M. Wuts, 3$^{rd}$ Edition, John Wiley & Sons, 1999. Alternatively, other reactions disclosed herein or known in the art will be recognized as having applicability for preparing other compounds of the various embodiments.

There are several different approaches to the synthesis of flavonols and in principle any of the known methodologies may be used to produce the compounds of the invention. We utilized a two-step reaction process namely, the Claisen-Schmidt condensation reaction, followed by the Algar-Flynn-Oyamada reaction (Scheme 1).

Scheme 1: Two-step reaction process for synthesis of flavonols.

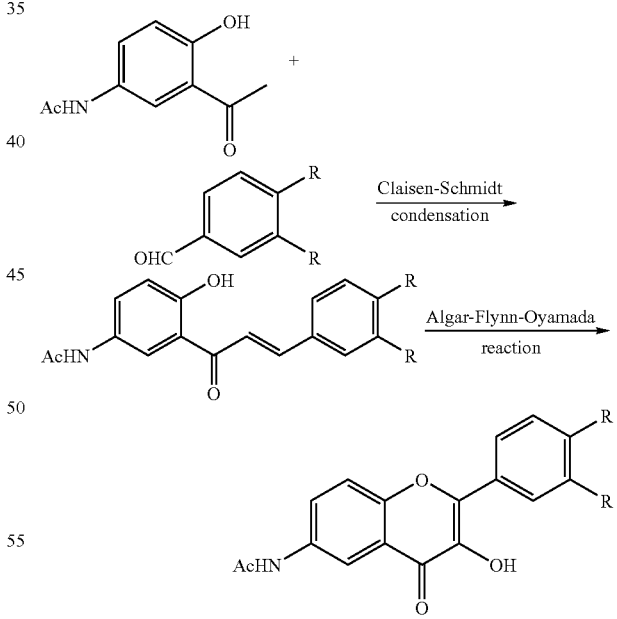

The first target flavonol 1 was a model compound for the development of the chemistry for the synthesis of more complex B-ring hydroxylated flavonols. While benzaldehyde was commercially available, 5-acetamido-2-hydroxyacetophenone was not and therefore had to be synthesized utilising the procedure outlined in Scheme 2. Thus, p-anisidine was acetylated by treatment with acetic anhydride in dichloromethane. Addition of petroleum spirits allowed isolation of 4-acetamidoanisole. Next, treatment of 4-acetamidoanisole with acetyl chloride and aluminium chloride effected Friedel-Crafts acylation. Subsequently, heating the reaction mixture at reflux resulted in demethylation, affording 5-acetamido-2-hydroxyacetophenone 4 in large amounts (20-30 g).

Scheme 2:

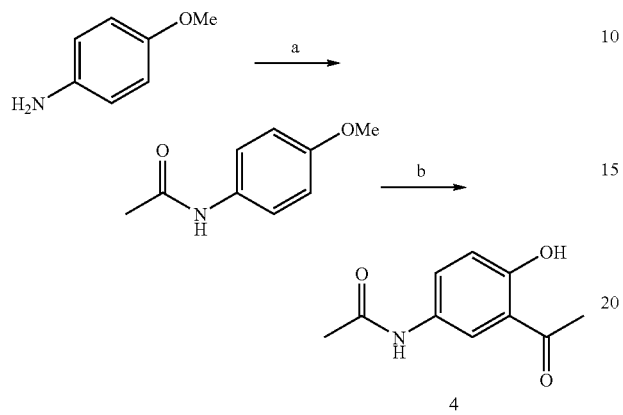

Reagents/conditions: (a) Ac$_2$O, CH$_2$Cl$_2$, 78%; (b) AlCl$_3$, AcCl, CH$_2$Cl$_2$, 96%.

With substantial amounts of 4 in hand, the next steps were to form the 6-acetamidoflavonol. Thus, the acetophenone 4 was treated with benzaldehyde and base to effect a Claisen-Schmidt condensation affording the chalcone 5 in 71% yield. The chalcone 5 was treated with alkaline hydrogen peroxide to enable an Algar-Flynn-Oyamada reaction, giving 6-acetamidoflavonol 6 in 50% yield. The next step was to unveil the 6-amino group of 6 to allow coupling with succinic anhydride for installation of the succinamic acid side chain. The 6-acetamidoflavonol 6 was treated with 5 M HCl in ethanol at reflux, followed by neutralization with aqueous ammonia to give 6-aminoflavonol.

With 6-aminoflavonol in hand the condensation with succinic anhydride was investigated. It was found that rather than form the amino flavonol, the crude HCl salt 7 of 6-aminoflavonol, after hydrolysis of the acetamide, could be readily isolated simply by diluting the reaction mixture with water. The crude salt 7 was treated with succinic anhydride in pyridine to afford the succinamic acid 1 in an excellent yield (42% from 5) (Scheme 3).

Scheme 3:

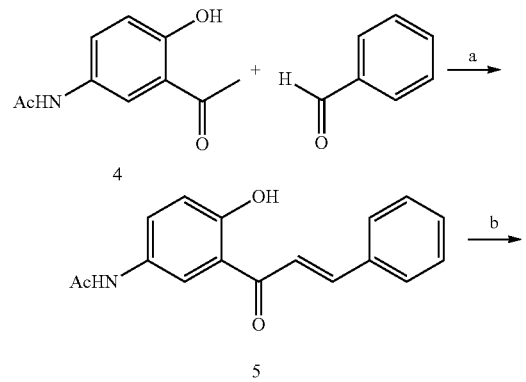

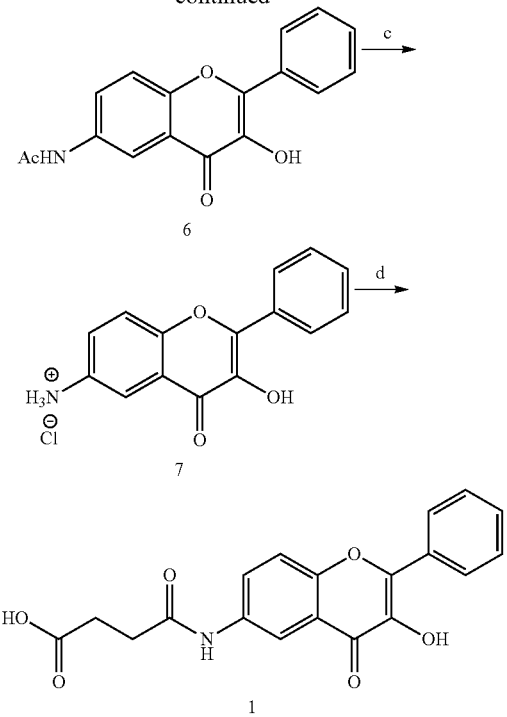

Reagents/conditions: (a) NaOH, EtOH, 71%; (b) NaOH, H$_2$O$_2$, EtOH, 50%;(c) 5 M HCl, EtOH; (d) succinic anhydride, pyridine, 42% over 2 steps.

Unfortunately the general synthetic scheme used in the formation of 1 was not to amenable to the formation of the compounds functionalised on the B ring. Installation of a p-methoxybenzyl protecting group was performed by refluxing a solution of 5-acetamido-2-hydroxyacetophenone 4 and p-methoxybenzyl chloride in the presence of K$_2$CO$_3$. Use of a common solvent, acetone, in the reaction resulted in low yields and long reaction times. When the solvent was changed to butanone, which boils 23° C. higher than acetone, the PMB ether 8 was obtained in an excellent yield (82%). With this protected acetophenone in hand, the Claisen-Schmidt condensation was investigated. Gratifyingly, treatment of the PMB ether 8 and 4-benzyloxybenzaldehyde with NaOH, under the conditions used previously for the synthesis of the model compound afforded the protected chalcone 9 in good yield (86%) (Scheme 4).

Scheme 4:

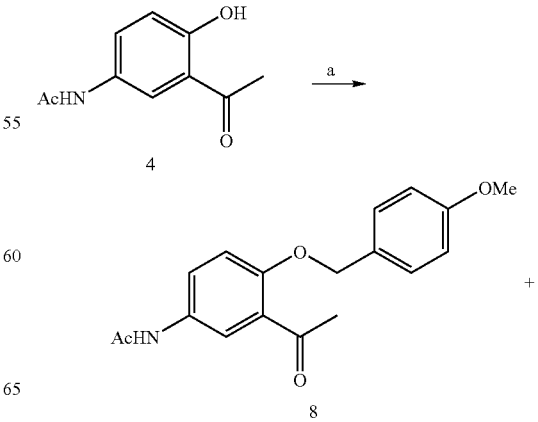

-continued

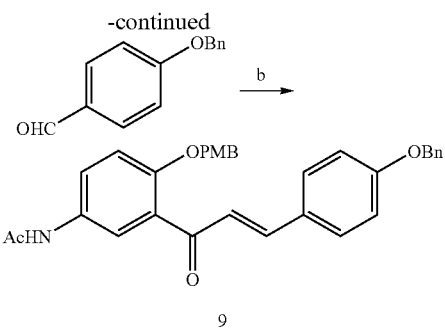

9

Reagents/conditions: (a) PMBCl, K$_2$CO$_3$, butanone, reflux, 82%; (b) NaOH, EtOH, 86%.

The next task was to selectively reveal the 2-hydroxyl of the PMB-chalcone 9, while keeping the benzyl and acetamide groups of the molecule intact. This was achieved by refluxing the protected chalcone 9 in aqueous HCl. This reaction had to be performed with care, as it was already known from the synthesis of the model compound I that aqueous HCl can also hydrolyze the acetamido group. Here, a lower concentration of HCl was used (2 M, rather than 5 M), and the reaction was continuously monitored by t.l.c. for completion. The crude deprotected product 10 was carried forward in the next step, the Algar-Flynn-Oyamada reaction, in a procedure similar to that used for the synthesis of 1, but with the inclusion of 1,4-dioxane to improve the solubility of starting materials. This gave the desired flavonol 11 in good yield (57% from 9) (Scheme 5).

Scheme 5:

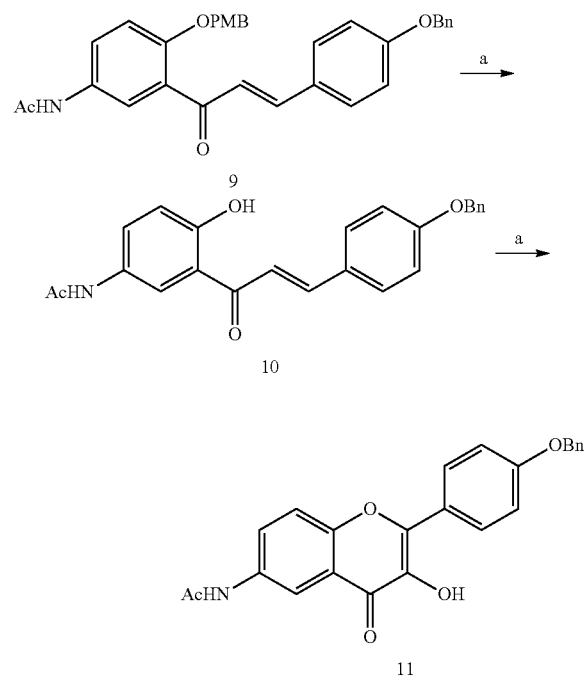

Reagents/conditions: (a) 2 M HCl, EtOH, 70° C., 1 h; (b) NaOH, H$_2$O$_2$, EtOH, 1,4-dioxane, 57% over 2 steps.

Refluxing the fully protected flavonol 11 in concentrated HCl and acetic acid resulted in clean conversion to the deprotected flavonol, isolated as the HCl salt 12. Finally, reaction of the crude salt 12 with succinic anhydride in pyridine, under the conditions that were used for the model compound I, afforded the succinamic acid derivative of 4'-hydroxyflavonol 2 (Scheme 6), which was purified by recrystallization from DMF/water.

Scheme 6:

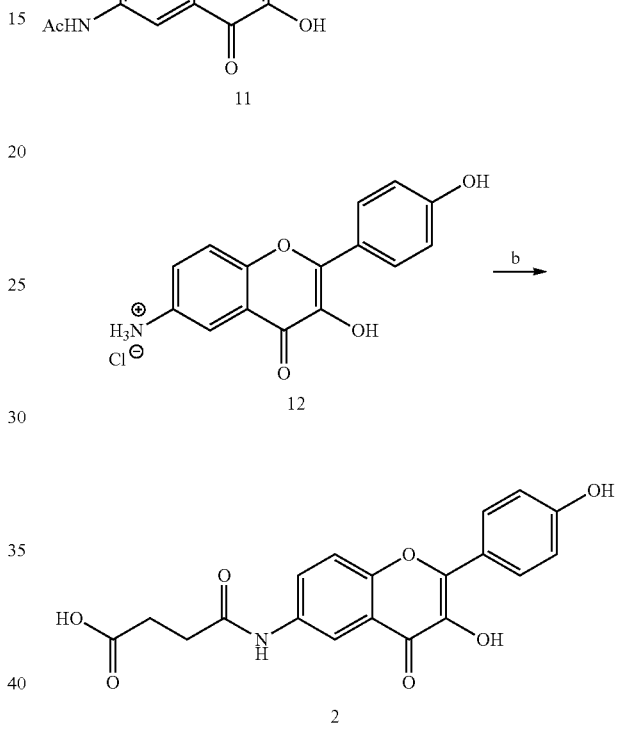

Reagents/conditions: (a) 36% HCl, AcOH, reflux, 2 h; (b) succinic anhydride, pyridine, 38% over 2 steps.

Using the procedure established for the synthesis of 2, the synthesis of the succinamic acid substituted 3',4'-dihydroxyflavonol 3 proved mostly uneventful. Thus, while the condensation of the protected acetophenone 8 with 3,4-dibenzyloxy-benzaldehyde did not proceed at room temperature, upon heating the mixture to 40° C., an excellent yield of the protected chalcone 13 was obtained (71%), emphasizing the advantage of protecting the 2-hydroxyl group of the acetophenone. The PMB group of the chalcone 13 was selectively removed by careful treatment with refluxing 2 M HCl in ethanol and the crude 2'-hydroxychalcone 14 treated immediately with alkaline hydrogen peroxide to effect an Algar-Flynn-Oyamada reaction, affording the flavonol 15 in 50% yield. The benzyl ethers and acetamido group of the flavonol 15 were hydrolyzed with concentrated aqueous HCl in acetic acid and the crude HCl salt 16 isolated by centrifugation. Finally, the succinamic acid moiety was introduced by treating the HCl salt 16 with succinic anhydride in pyridine to afford the target compound 3 in 19% yield (Scheme 7), purified by recrystallization from DMF/water.

Scheme 7:

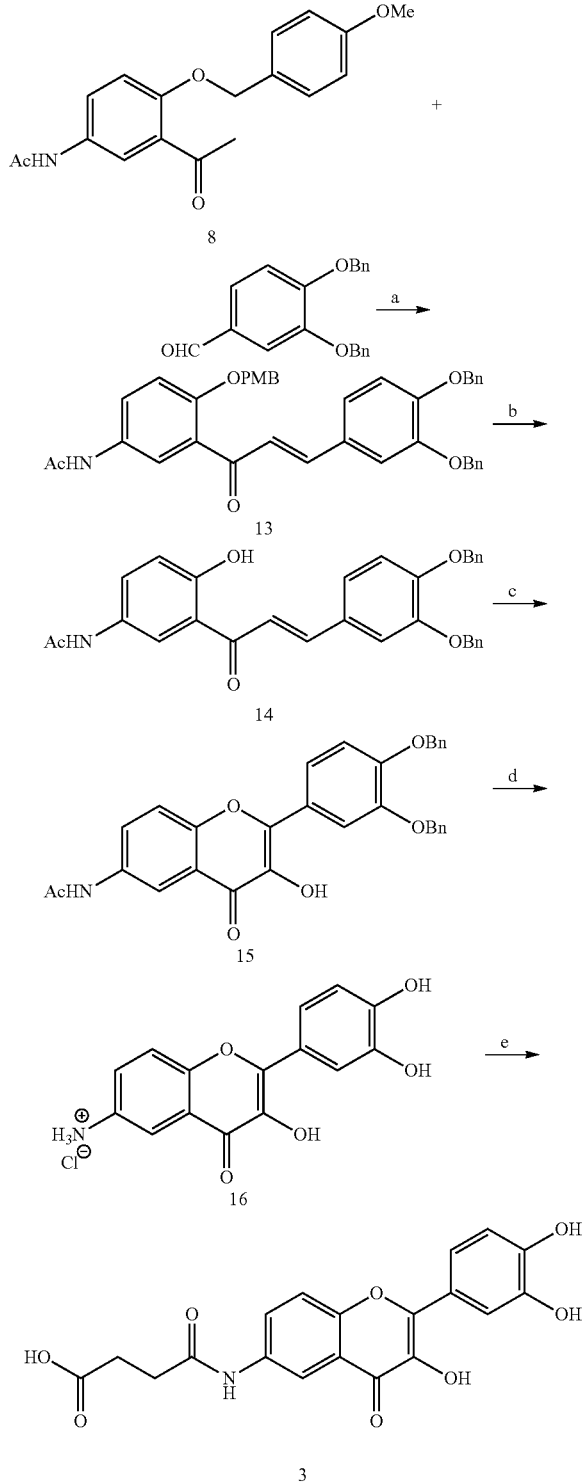

Reagents/conditions: (a) NaOH, EtOH, 40° C., 71%; (b) 2 M HCl, EtOH, 70° C., 1 h; (c) H₂O₂, NaOH, EtOH, 1,4-dioxane, 50% over 2 steps; (d) 36% HCl, AcOH, reflux, 3 h; (e) succinic anhydride, pyridine, 19% over 2 steps.

In order to probe the generality of the modifications it was decided to make an analog of quercetin, another active flavonol. This was synthesised as shown in Scheme 8.

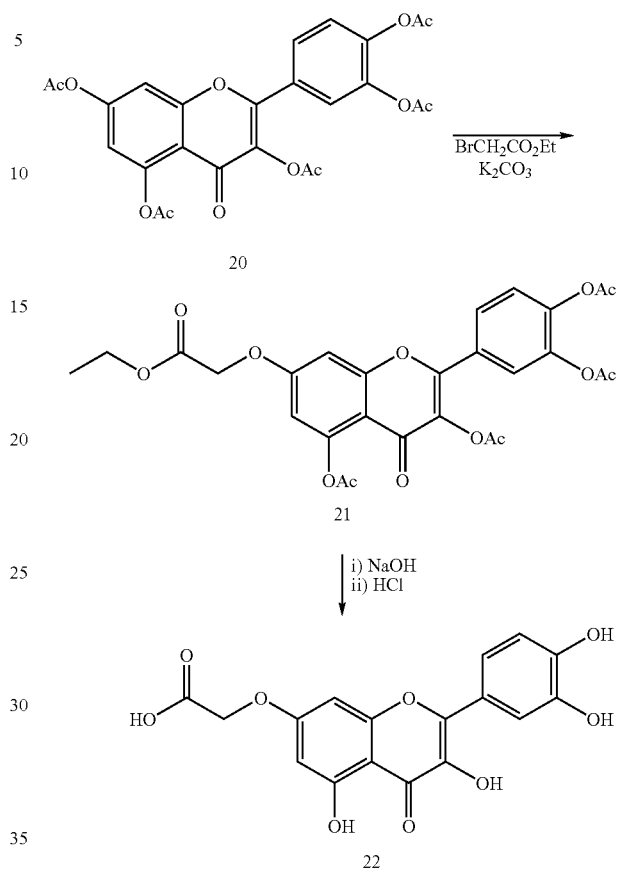

Thus quercetin pentaacetate (20) was subjected to alkylation conditions to selectively alkylate the hydroxyl moiety at the 7 position. Saponification of the acetate groups and the methyl ester lead to the formation of quercetin 7-O-acetic acid.

EXAMPLES

Reagents useful for synthesizing compounds may be obtained or prepared according to techniques known in the art.

In the examples described below, unless otherwise indicated, all temperatures in the following description are in degrees Celsius and all parts and percentages are by weight, unless indicated otherwise.

Various starting materials and other reagents were purchased from commercial suppliers, such as Aldrich Chemical Company or Lancaster Synthesis Ltd., and used without further purification, unless otherwise indicated. Tetrahydrofuran (THF) and N,N-dimethylformamide (DMF) were purchased from Aldrich in SureSeal bottles and used as received. All solvents were purified by using standard methods in the art, unless otherwise indicated.

Chemistry

General Methods

Thin layer chromatography (t.l.c) was performed on aluminium sheets pre-coated with Merck Silica Gel 60, using mixtures of ethyl acetate and petroleum spirits, or mixtures of diethyl ether and dichloromethane. Detection was achieved by irradiation with UV light. NMR data was obtained on Varian Unity Plus 400 or 500 instruments in solutions of $d_6$-DMSO using residual solvent as internal standard (δ 2.50 ppm for $^1$H, δ 39.51 ppm for $^{13}$C) or in CDCl$_3$ using TMS as an internal standard (δ 0.00 ppm). Evaporation of solvents was performed under reduced pressure using a rotary evaporator. Elemental analyses were performed by CMAS (Belmont, Victoria). Melting points were obtained using an Electrothermal melting point apparatus or Riechert-Jung Hot-stage melting point apparatus and in the latter case are corrected. Low resolution mass spectra were obtained by electrospray ionization using a triple-quad Quattro II instrument (The University of Melbourne).

Example 1

4-Acetamidoanisole

Acetic anhydride (16.0 mL, 169 mmol) was added dropwise over 1 h to a mixture of p-anisidine (20.0 g, 162 mmol) and dichloromethane (60 mL), with moderation by cooling in a water bath. The mixture was stirred at room temperature for 1 h, during which time a solid formed. Petroleum spirit (190 mL) was added, and the mixture was stirred for a further 1 h. The mixture was filtered and washed with petroleum spirit to afford 4-acetamidoanisole as a pale grey solid (25.8 g, 96%), m.p. 127-128° C. $^1$H NMR (399.7 MHz, CDCl$_3$) δ 2.13, 3.78 (2 s, 2×3H, 2×CH$_3$); 6.83 (app. d, 2H, J=8.8 Hz, BB'); 7.38 (app. d, 2H, J=8.8 Hz, AA'); 7.59 (br s, 1H, NH).

Example 2

5-Acetamido-2-hydroxyacetophenone (4)

Aluminium chloride (56.0 g, 420 mmol) was added in four portions over 45 min to a mixture of 4-acetamidoanisole (20.0 g, 121 mmol) and acetyl chloride (25.8 mL, 363 mmol) in dichloromethane (190 mL). After addition of the first portion, the mixture became clear, and after addition of all four portions, a suspension formed again. The mixture was then heated at reflux for 4.5 h, after which it was cooled and poured into ice/water and vigorously stirred for 30 min. The resultant slurry was filtered and washed with water and the solid was dried to afford the acetophenone (4) as a light green powder (18.2 g, 78%), m.p 163-167° C. $^1$H NMR (399.7 MHz, CDCl$_3$) δ 2.18 (s, 3H, CH$_3$CON); 2.62 (s, 3H, CH$_3$COAr); 6.93 (d, 1H, $J_{3,4}$ 9.0 Hz, H3); 7.34 (dd, 1H, $J_{3,4}$ 9.0, $J_{4,6}$ 2.6 Hz, H4); 8.17 (d, 1H, $J_{4,6}$ 2.6 Hz, H6); 12.10 (s, 1H, NH).

Example 3

5'-Acetamido-2'-hydroxychalcone (5)

Aqueous NaOH (12 mL of 25.2 g/100 mL) was added to a mixture of 5-acetamido-2-hydroxyacetophenone (4) (1.00 g, 5.18 mmol) and benzaldehyde (0.79 mL, 7.77 mmol) in ethanol (12 mL), and the mixture was stirred at room temperature for 6 h. The mixture was acidified with 30% aqueous acetic acid, with cooling on ice. The mixture was stirred for 1 h and filtered to afford the chalcone (5) as a brown solid (1.20 g, 82%), m.p. 162-165° C. $^1$H NMR (399.7 MHz, CDCl$_3$) δ 2.21 (s, 3H, CH$_3$); 6.98 (d, 1H, $J_{3',4'}$ 8.8 Hz, H3'); 7.34 (dd, 1H, $J_{3',4'}$ 8.8, $J_{4',6'}$ 2.4 Hz, H4'); 7.41-7.44 (m, 3H, H3,4,5); 7.61-7.69 (m, 3H, H2,6,C=CH); 7.92 (d, 1H, $J_{trans}$ 15.6 Hz, CH=C); 8.41 (d, 1H, $J_{4',6'}$, 2.4 Hz, H3').

Example 4

6-Acetamidoflavonol (6)

Aqueous hydrogen peroxide (30% w/v, 4 mL) was added to an ice-cold suspension of 5'-acetamido-2'-hydroxychalcone (5) (2.00 g, 7.11 mmol) and 1 M NaOH (20 mL) in ethanol (60 mL). The mixture was allowed to warm to room temperature and was vigorously stirred overnight. The mixture was acidified with 1 M HCl and the precipitate formed was collected by filtration to afford the flavonol (6) as a bright yellow powder (1.04 g, 50%), m.p. 241-242° C. $^1$H NMR (399.7 MHz, $d_6$-DMSO) δ 2.10 (s, 3H, CH$_3$); 7.48-7.59 (m, 3H, H3',4',5'); 7.73 (d, 1H, $J_{7,8}$ 9.2 Hz, H8); 7.89 (dd, 1H, $J_{5,7}$ 2.8, $J_{7,8}$ 9.2 Hz, H7); 8.21 (app. d, 2H, J=7.6 Hz, H2',6'); 8.44 (d, 1H, $J_{5,7}$ 2.8 Hz, H5), 9.60 (br s, 1H, OH); 10.28 (s, 1H, NH).

Example 5

6-Aminoflavonol

Aqueous HCl (5 M, 20 mL) was added to a suspension of 6-acetamidoflavonol (6) (1.00 g, 3.39 mmol) in ethanol (30 mL) and the mixture was heated under reflux for 1.5 h. The mixture was cooled and made basic with aqueous NH$_3$ (litmus) and the precipitate formed was collected by filtration to afford 6-aminoflavonol as a bright yellow powder (0.437 g, 51%), m.p. 211-212° C. $^1$H NMR (399.7 MHz, $d_6$-DMSO) δ 5.48 (s, 1H, NH); 7.08 (dd, 1H, $J_{5,7}$ 2.8, $J_{7,8}$ 9.2 Hz, H7); 7.14 (d, 1H, $J_{5,7}$ 2.8 Hz, H5); 7.47-7.57 (m, 4H, H3',4',5',8); 8.17 (app. d, 2H, J=7.6 Hz, H2',6'); 8.62 (br s, 1H, OH).

Example 6

6-(Hydroxycarbonylethylcarbonylamino)flavonol (1)

Method A: A mixture of 6-aminoflavonol (100 mg, 0.395 mmol) and succinic anhydride (47 mg, 0.47 mmol) in pyridine (2 mL) was stirred at room temperature for 4 h. Water (1 mL) was added and the mixture was acidified with 2 M HCl. The resulting suspension was filtered to afford the succinamic acid (1) as a yellow solid, which was recrystallised from THF/petroleum spirits (72.0 mg, 52%).

Method B: A mixture of aqueous HCl (5 M, 1 mL) and 6-acetamidoflavonol (0.50 mg, 0.169 mmol) in ethanol (1.5 mL) was heated under reflux for 1.5 h. The mixture was cooled and diluted with water and the precipitate that formed was collected by filtration to afford the hydrochloride salt as a bright yellow powder. The crude product and succinic anhydride (14.1 mg, 0.141 mmol) was dissolved in pyridine (2 mL), and the mixture was stirred at room temperature for 4 h. Water (1 mL) was added and the mixture was acidified with 2 M HCl. The mixture was left to stand at room temperature for 30 min, and the resulting suspension was filtered and recrystallised from THF/petroleum spirits to afford the succinamic acid (1) as a yellow powder (24.5 mg, 42%), m.p. 220-223° C. Anal. Calc. for C$_{19}$H$_{15}$NO$_6$: C, 64.59; H, 4.28; N, 3.96. Found: C, 64.51; H, 4.19; N, 4.08. $^1$H NMR (399.7 MHz, $d_6$-DMSO) δ 2.55-2.61 (m, 4H, CH$_2$CH$_2$); 7.49-7.59 (m, 3H, H3',4',5'); 7.73 (d, 1H, $J_{7,8}$ 9.2 Hz, H8); 7.87 (dd, 1H, $J_{5,7}$ 2.8, $J_{7,8}$ 9.2 Hz, H7); 8.20 (app. d, 2H, J=8.4 Hz, H2',6'); 8.47 (d, 1H, $J_{5,7}$ 2.8 Hz, H5); 9.61 (br s, 1H, OH); 10.31 (s, 1H, NH); 12.18 (br s, 1H, CO$_2$H).

Example 7

5-Acetamido-2-(4-methoxybenzyloxy)acetophenone (8)

A mixture of 5-acetamido-2-hydroxyacetophenone (4) (3.00 g, 15.5 mmol), 4-methoxybenzyl chloride (3.20 mL, 31.1 mmol) and $K_2CO_3$ (3.21 g, 23.3 mmol) in butanone (45 mL) was heated under reflux overnight. The mixture was filtered and the filtrate was concentrated in vacuo, giving a yellow residue. The residue was triturated with petroleum spirit and immediately recrystallised from THF/petroleum spirit to afford the protected acetophenone 8 as a white powder (4.02 g, 82%), m.p. 169-171° C. Anal. Calcd. for $C_{18}H_{19}NO_4$: C, 68.99; H, 6.11; N, 4.47. Found: C, 68.86; H, 6.19; N, 4.53%. $^1$H NMR (399.7 MHz, CDCl$_3$) δ 2.16 (s, 3H, CH$_3$CON); 2.57 (s, 3H, CH$_3$COAr); 3.83 (s, 3H, CH$_3$O); 5.08 (s, 2H, CH$_2$); 6.92 (d, 2H, J=8.4 Hz, H2',6'); 7.02 (d, 1H, $J_{3,4}$ 8.8 Hz, H3); 7.35 (app. d, 2H, J=8.4 Hz, H3',5'); 7.52 (d, 1H, $J_{4,6}$ 3.2 Hz, H6); 7.97 (dd, 1H, $J_{3,4}$ 8.8, $J_{4,6}$ 3.2 Hz, H4). $^{13}$C NMR (100.5 MHz, CDCl$_3$) δ 24.58, 32.45, 55.52, 71.03 (4C, CH$_2$, OCH$_3$, 2×CH$_3$); 113.86, 114.28, 122.09, 126.52, 128.30, 128.43, 129.59, 131.47, 155.23, 159.82 (10C, Ar); 168.63, 199.52 (2C, 2×C=O).

Example 8

5'-Acetamido-4-benzyloxy-2'-(4-methoxybenzyloxy) chalcone (9)

A mixture of aqueous NaOH (25.5 mL of 25.2 g/100 mL), the protected acetophenone (8) (3.00 g, 9.57 mmol) and 4-benzyloxybenzaldehyde (2.03 g, 9.57 mmol) in ethanol (25.5 mL) was stirred at room temperature overnight. The mixture was filtered to afford the protected chalcone (9) as a light yellow solid (3.54 g, 73%), m.p. 201-202° C. Anal. Calcd. for $C_{32}H_{29}NO_5$: C, 75.72; H, 5.76; N, 2.76. Found: C, 75.60; H, 5.74; N, 2.73%. $^1$H NMR (399.7 MHz, CDCl$_3$) δ 2.17 (s, 3H, CH$_3$CON); 3.77 (s, 3H, CH$_3$O); 5.06, 5.09 (2 s, 2×2H, 2×CH$_2$Ar); 6.82 (app. d, 2H, J=8.8 Hz, BB'); 6.88 (app. d, 2H, J=8.8 Hz, BB'); 7.04 (d, 1H, $J_{3',4'}$ 9.0 Hz, H3'); 7.27 (app. d, 2H, J=8.8 Hz, AA'); 7.31-7.45 (m, 8H, AA', C=CH,Ph); 7.51 (d, 1H, $J_{4',6'}$ 2.8 Hz, H6'); 7.58 (d, 1H, $J_{trans}$ 15.6 Hz, C=CH); 7.98 (dd, 1H, $J_{3',4'}$ 9.0, $J_{4',6'}$ 2.8 Hz, H4'). $^{13}$C NMR (100.5 MHz, d$_6$-DMSO) δ 23.85, 55.05 (2C, 2×CH$_3$); 69.38, 70.13 (2C, 2×CH$_2$); 79.20, 113.82, 113.91, 115.14, 120.54, 123.94, 124.80, 127.39, 127.79, 128.00, 128.45, 128.53, 129.94, 130.30, 132.73, 136.70, 142.17, 153.06, 159.10, 160.24 (20C, Ar, CH=CH); 168.06, 190.69 (2C, 2×C=O).

Example 9

6-Acetamido-4'-benzyloxyflavonol (11)

A solution of 4-methoxybenzyloxychalcone (9) (1.20 g, 1.70 mmol) in aqueous HCl (2 M, 66 mL) and ethanol (290 mL) was heated at reflux for 1 h. The mixture was cooled to room temperature, and evaporated in vacuo to approximately half the volume. The resultant suspension was filtered to afford the crude deprotected chalcone (10) as a yellow solid. The crude deprotected chalcone was dissolved in 1,4-dioxane (19.2 mL), ethanol (24 mL) and NaOH (5.4% w/v, 7.8 mL). The resultant solution was cooled in an ice bath and H$_2$O$_2$ (30%, 1.2 mL) was added. The solution was stirred at 0° C. for 2 h, and subsequently at room temperature overnight. The solution was then acidified with 2 M HCl and the precipitate that formed was filtered, then recrystallised from THF/petroleum spirit to afford the flavonol (11) as a bright yellow solid (341 mg, 36%), m.p. 255-258° C. Anal. Calcd. for $C_{24}H_{19}NO_5$: C, 71.81; H, 4.77; N, 3.49. Found: C, 71.90; H, 4.80; N, 3.51%. $^1$H NMR (499.7 MHz, d$_6$-DMSO) δ 2.09 (s, 3H, CH$_3$); 5.19 (s, 2H, CH$_2$); 7.19 (app. d, 2H, J=9.0 Hz, H2',6'); 7.32-7.50 (m, 5H, Ph); 7.69 (d, 1H, $J_{7,8}$ 9.0 Hz, H8); 7.86 (dd, 1H, $J_{5,7}$ 2.5, $J_{7,8}$ 9.0 Hz, H7); 8.18 (app. d, 2H, J=9.0 Hz, H3',5'); 8.41 (d, 1H, $J_{5,7}$ 2.5 Hz, H5); 10.28 (br s, 1H, NH). $^{13}$C NMR (100.5 MHz, d$_6$-DMSO) δ 24.00 (1C, CH$_3$); 69.37 (1C, CH$_2$); 112.63, 114.88, 118.83, 121.41, 123.84, 125.27, 127.84, 127.98, 128.49, 129.35, 135.89, 136.68, 137.93, 145.41, 150.45, 159.48 (16C, Ar); 168.54, 172.46 (2C, 2×C=O).

Example 10

4'-Hydroxy-6-(hydroxycarbonylethylcarbonylamino) flavonol (2)

A mixture of the protected flavonol (11) (600 mg, 1.49 mmol) in aqueous HCl (36%, 38 mL) and acetic acid (38 mL) was heated under reflux for 2 h. The mixture was then cooled on ice and diluted with water. The resulting suspension was centrifuged and the collected solid washed with water, then freeze-dried to afford the salt as a crude yellow solid (457 mg). A mixture of the crude yellow product and succinic anhydride (179 mg, 1.79 mmol) in pyridine was stirred at room temperature for 4 h. Water (1 mL) was added and the mixture was acidified with 2 M HCl. The mixture was left to stand at room temperature for 30 min, and the resulting suspension was centrifuged and the collected solid was washed with water, freeze-dried and recrystallised from DMF/water to afford the succinamic acid (2) as a brown powder (211 mg, 38.2%), m.p. 256-257° C. Anal. Calcd. for $C_{19}H_{16}NO_7 \cdot \frac{1}{2}H_2O$: C, 60.32; H, 4.26; N, 3.70. Found: C, 59.99; H, 4.53; N, 3.90. $^1$H NMR (399.7 MHz, d$_6$-DMSO) δ 2.55-2.60 (m, 4H, CH$_2$CH$_2$); 6.93 (app. d, 2H, J=9.2 Hz, H3',5'); 7.69 (d, 1H, $J_{7,8}$ 8.8 Hz, H8); 7.85 (dd, 1H, $J_{5,7}$ 2.8, $J_{7,8}$ 8.8 Hz, H7); 8.09 (app. d, 2H, J=9.2 Hz, H2',6'); 8.43 (d, 1H, $J_{5,7}$ 2.8 Hz, H5); 9.33 (s, 1H, NH); 10.11, 10.31 (2 br s, 2×1H, 2×OH); 12.21 (br s, 1H, CO$_2$H). $^{13}$C NMR (100.5 MHz, d$_6$-DMSO) δ 25.16, 28.78 (2C, CH$_2$CH$_2$); 31.06, 67.05, 112.65, 115.46, 118.80, 121.45, 122.06, 125.11, 129.55, 135.80, 137.57, 146.01, 150.38, 159.11 (14C, Ar); 170.40, 172.33, 173.86 (3C, 3×C=O).

Example 11

5'-Acetamido-3,4-dibenzyloxy-2'-(4-methoxybenzyloxy)-chalcone (13)

A mixture of aqueous NaOH (3.8 mL of 25.2 g/100 mL), the protected acetophenone (8) (500 mg, 1.60 mmol) and 3,4-dibenzyloxybenzaldehyde (500 mg, 1.60 mmol) in ethanol (3.8 mL) was stirred at 40° C. overnight. The mixture was cooled, then filtered, and recrystallised from THF/petroleum spirits to afford the protected chalcone (13) as a yellow solid (692 mg, 71%), m.p. 145-146° C. Anal. Calcd. for $C_{39}H_{35}NO_6$: C, 76.33; H, 5.75; N, 2.28. Found: C, 76.36; H, 5.81; N, 2.19%. $^1$H NMR (399.7 MHz, CDCl$_3$) δ 2.17 (s, 3H, CH$_3$CON); 3.69 (s, 3H, CH$_3$O); 5.03, 5.06, 5.20 (3 s, 3×2H, 3×CH$_2$); 6.77 (app. d, 2H, J=8.4 Hz, BB'); 6.85 (d, 1H, $J_{5,6}$ 8.2 Hz, H5); 6.92 (dd, 1H, $J_{2,6}$ 2.4, $J_{5,6}$ 8.2 Hz, H6); 7.04 (app. d, 2H, H2,3'); 7.26-7.48 (m, 14H, H6',2×Ph, AA', C=CH); 7.51 (d, 1H, $J_{trans}$ 15.6 Hz, C=CH); 7.95 (dd, 1H, $J_{3',4'}$ 8.2, $J_{4',6'}$ 2.4 Hz, H4'). $^{13}$C NMR (100.5 MHz, d$_6$-DMSO) δ 23.88, 54.98, 69.91, 70.01, 70.14 (5C, 3×CH$_2$,2×CH$_3$); 113.65, 113.71, 113.88, 113.97, 120.37, 123.08, 123.65, 125.30, 127.53, 127.67, 127.77, 127.90, 128.45, 128.50, 128.56, 129.06, 129.51, 132.78, 136.93, 137.07, 142.74, 148.31, 150.46, 152.73, 158.96 (25C, Ar, CH=CH); 168.15, 191.48 (2C, 2×C=O).

Example 12

6-Acetamido-3',4'-dibenzyloxyflavonol (15)

A solution of 4'-methoxybenzyloxychalcone (13) (300 mg, 0.489 mmol) in aqueous HCl (2 M, 16 mL) and ethanol (66 mL) was heated at reflux for 1 h. The mixture was cooled to room temperature, and evaporated in vacuo to approximately half the volume. The resultant suspension was filtered to afford the crude deprotected chalcone (14) as a dark yellow solid. The deprotected chalcone was dissolved in 1,4-dioxane (4.8 mL), ethanol (6 mL) and NaOH (5.4% w/v, 1.9 mL) and the resultant solution was cooled in an ice bath and H$_2$O$_2$ (30%, 0.3 mL) was added. The solution was stirred at 0° C. for 2 h, and subsequently at room temperature overnight. The solution was then acidified with 2 M HCl and the precipitate that formed was filtered, and then recrystallised from THF/petroleum spirits to afford the flavonol (15) as a yellow solid (136 mg, 55%), m.p. 229-230° C. Anal. Calcd. for C$_{31}$H$_{25}$NO$_6$: C, 73.36; H, 4.96; N, 2.76. Found: C, 73.38; H, 4.98; N, 2.68%. $^1$H NMR (399.7 MHz, d$_6$-DMSO) δ 2.09 (s, 3H, CH$_3$); 5.21, 5.24 (2 s, 2×2H, 2×CH$_2$); 7.26 (d, 1H, J$_{5',6'}$ 8.8 Hz, H5'); 7.33-7.52 (m, 11H, 2×Ph); 7.71 (d, 1H, J$_{7,8}$ 9.2 Hz, H8); 7.84-7.92 (m, 3H, H2',6',7); 8.40 (d, 1H, J$_{5,7}$ 2.4 Hz, H5); 9.48 (br s, 1H, OH); 10.27 (s, 1H, NH). $^{13}$C NMR (100.5 MHz, d$_6$-DMSO) δ 24.03 (1C, CH$_3$); 69.91, 70.43, 112.65, 112.69, 113.79, 118.89, 121.38, 121.91, 124.06, 125.32, 135.91, 136.88, 137.08, 138.14, 145.14, 147.77, 149.77, 150.42 (18C, Ar); 168.59, 172.47 (2C, 2×C=O).

Example 13

3',4'-Dihydroxy-6-(hydroxycarbonylethylcarbonylamino)flavonol (3)

A mixture of the protected flavonol (15) (500 mg, 0.985 mmol) in aqueous HCl (36%, 37 mL) and acetic acid (37 mL) was heated under reflux for 3 h. The mixture was then cooled on ice and diluted with water. The resulting suspension was centrifuged and the collected solid washed with water, then freeze-dried to afford the salt as a crude yellow solid (322 mg). A mixture of the crude yellow product and succinic anhydride (118 mg, 1.18 mmol) in pyridine was stirred at room temperature for 4 h. Water (1 mL) was added and the mixture was acidified with 6 M HCl. The mixture was left to stand at room temperature for 30 min, and the resulting suspension was centrifuged, and the collected solid was washed with water, freeze-dried and recrystallised from DMF/water to afford the succinamic acid (3) as a yellow powder (70.0 mg, 19%), m.p 257-258° C. $^1$H NMR (399.7 MHz, d$_6$-DMSO) δ 2.54-2.60 (m, 4H, CH$_2$CH$_2$); 6.89 (d, 1H, J$_{5',6'}$ 8.5 Hz, H5'); 7.57 (dd, 1H, J$_{2',6'}$ 2.5, J$_{5',6'}$ 8.5 Hz, H6'); 7.66 (d, 1H, J$_{7,8}$ 9 Hz, H8); 7.73 (d, 1H, J$_{2',6'}$ 2.5 Hz, H2'); 7.85 (dd, 1H, J$_{5,7}$ 2.5, J$_{7,8}$ 9.0 Hz, H7); 8.43 (d, 1H, J$_{5,7}$ 2.5 Hz, H5); 9.29, 9.32, 9.59 (3 br s, 3×1H, 3×OH); 10.29 (s, 1H, NH); 12.20 (br s, 1H, CO$_2$H). $^{13}$C NMR (100.5 MHz, d$_6$-DMSO) δ 28.83, 31.11 (2C, CH$_2$CH$_2$); 112.7, 115.25, 115.65, 118.76, 120.00, 121.43, 122.39, 125.17, 135.80, 137.67, 145.12, 146.04, 147.63, 150.38 (14C, Ar); 170.46, 172.32, 173.93 (3C, 3×C=O). Low resolution mass spectrum (ESI) m/z 384.4 [C$_{19}$H$_{15}$NO$_8$ (M-H)$^+$ requires 384.08].

Example 14

Penta-O-acetylquercetin (20)

A suspension of quercetin (10.0 g, 33.2 mmol) in acetic anhydride (50 mL, 530 mmol) and pyridine (25 mL) was stirred at room temperature for 15 min. The mixture was poured into ice-water (500 mL) and stirred for 15 min, and the solid that formed was collected by vacuum filtration and washed with ice-cold ethanol (20 mL). The crude material was recrystallised from EtOAc/petroleum spirits to afford the pentaacetate as pale beige needles (12.3 g, 72%), m.p. 195-196° C. $^1$H NMR (399.7 MHz, CDCl$_3$) d 2.32, 2.33, 2.34, 2.43 (4 s, 15H, 5×Me); 6.88, 7.33 (2 d, J$_{6,8}$ 2.4 Hz, H6,8); 7.35 (d, J$_{5',6'}$ 8.4 Hz, H5'); 7.7 (d, J$_{2',6'}$ 2.0 Hz, H2'); 7.63 (dd, H6'). $^{13}$C NMR (100.5 MHz, CDCl$_3$) δ 20.43, 20.56, 20.94, 21.06 (5C, Me);108.94, 113.82, 114.63, 123.75, 123.86, 126.33, 127.62, 133.93, 142.09, 144.29, 150.26, 153.65, 154.17, 156.73 (14C, Ar); 167.71, 167.78, 169.19, 169.95 (6C, C=O).

Example 15

3,3',4',5-Tetra-O-acetyl-7-O-(ethoxycarbonyl)methylquercetin (21)

A mixture of pentaacetate (20) (1.02 g, 1.98 mmol), ethyl bromoacetate (0.97 mL, 8.75 mmol), potassium iodide (0.1 g, 0.60 mmol), anhydrous potassium carbonate (2.5 g) and anhydrous acetone (25 mL) was heated under reflux for 19 h under an atmosphere of nitrogen. The mixture was filtered to remove undissolved salts and the filtrate concentrated to yield an oil. The crude residue was purified by flash chromatography (40% EtOAc/toluene) and recrystallised from EtOAc/petroleum spirits to afford the ethyl ester as a colourless crystalline powder (0.322 g, 29%), m.p. 151-152° C. $^1$H NMR (399.7 MHz, CDCl$_3$) δ 1.31 (t, 3H, J=7.2 Hz, CH$_2$CH$_3$); 2.17, 2.33, 2.43 (3 s, 12H, 4×Me); 4.29 (q, 2H, CH$_2$CH$_3$); 4.71 (s, 2H, CH$_2$CO); 6.69, 6.81 (2 d, J$_{6,8}$ 2.4 Hz, H6,8); 7.34 (d, J$_{5',6'}$ 8.4 Hz, H5'); 7.67 (d, J$_{2',6'}$ 2.0 Hz, H2'); 7.70 (dd, H6').

Example 16

7-O-(Hydroxycarbonyl)methylquercetin (22)

Aqueous sodium hydroxide (10%, 0.25 mL) was added to a suspension of the ethyl ester (21) (252 mg, 0.453 mmol) in methanol (2.5 mL) and the mixture was heated in a water bath (60° C.) for 5 min. Water (1 mL) was then added and heating continued for 5 min. The mixture was acidified with concentrated hydrochloric acid (0.2 mL) and heated for a further min. The crystalline solid that separated was collected and recrystallised (EtOAc/petroleum spirits) to yield the acid as a yellow crystalline powder (54.0 mg, 33%), m.p. 241-243° C. (dec.). $^1$H NMR (399.7 MHz, CD$_3$OD) δ 1.29 (s, 2H, CH$_2$); 6.28, 6.49 (2 d, J$_{6,8}$ 2.4 Hz, H6,8); 6.86 (d, J$_{5',6'}$ 8.4 Hz, H5'); 7.62 (dd, J$_{2',6'}$ 2.4 Hz, H6'); 7.73 (d, H2'). $^{13}$C NMR (100.5 MHz, CD$_3$OD) δ 52.42 (CH$_2$); 93.16, 98.42, 105.47, 115.75, 115.87, 121.45, 123.57, 137.23, 145.85, 148.17, 148.57, 157.43, 161.93, 164.54 (Ar); 170.18, 176.98 (2×C=O). High resolution mass spectrum (ESI) m/z 397.0525 [C$_{17}$H$_{10}$KO$_9$ (M+K)$^-$ requires 396.9962].

Pharmacology

Drugs and Chemicals Used

Acetylcholine perchlorate was obtained from BDH Chemicals (Poole, Dorset, England). Phenylephrine and propranolol was purchased from Sigma-Aldrich Pty. Ltd. (Castle Hill, NSW, Australia). DiOHF was purchased from Indofine Chemical Co. Inc. (Belle Mead, N.J., U.S.A.). All other flavonols were synthesized in this study. 046619 was purchased from Cayman Chemical (Ann Arbor, Mich., U.S.A.). All chemicals were dissolved in distilled water, except the following. DiOHF was dissolved in 10% dimethyl sulphoxide (DMSO), 90% methanol, with subsequent dilutions in 50% methanol ($10^{-3}$ M), and distilled water ($10^{-4}$-$10^{-7}$ M). Succinamic acid-substituted flavonols were dissolved in 0.1 M $Na_2CO_3$ as a stock solution (B and C at $10^{-1}$ and D at $10^{-2}$ M), and further diluted in distilled water as required.

Preparation of Rat Aortic Rings

Male Sprague-Dawley rats (200-400 g) were euthanised by exposure to 80% $CO_2$, 20% $O_2$, and their chests opened to isolate the thoracic aortae. After the removal of superficial connective tissues, the aorta was cut into ring segments, of approximately 2-3 mm in length. The aortic rings were then mounted between two stainless steel wires, one of which was linked to an isometric force transducer connected to a chart recorder, and the other end anchored to a glass rod submerged in a standard 10 mL organ bath. The organ bath was filled with Krebs-bicarbonate solution [composition (mM): NaCl, 118.0; KCl, 4.7; $KH_2PO_4$, 1.2; $MgSO_4.7H_2O$, 1.2; glucose, 5.0; $NaHCO_3$, 25.0; $CaCl_2.2H_2O$, 2.5]. The bath medium was maintained at 37° C., pH 7.4 and continuously aerated with 95% $O_2$, 5% $CO_2$.

Equilibration of Aortic Rings & Testing of Endothelial Integrity

Aortic rings were equilibrated for 1 h at a resting tension of 1 g, then were precontracted with an isotonic, high potassium physiological salt solution (KPSS) in which all of the NaCl of the normal Krebs solution was replaced with KCl (122.7 mM), so as to achieve maximal contraction. The solution was then washed out and replaced with normal Krebs solution. After re-equilibration, the rings were submaximally contracted with phenylephrine (PE, $10^{-8}$-$10^{-7}$ M) and endothelial integrity was tested by a single dose of acetylcholine (Ach, $10^{-5}$ M). Only rings that responded to Ach ($\geq$90% relaxation) were judged endothelium intact and were used in the subsequent experiments. The aortic rings were then re-equilibrated (15 min) before the subsequent experiment.

Effect of Flavonols on Phenylephrine-Induced Vasoconstriction

Aortic rings were incubated with a β-adrenoceptor antagonist, propranolol ($10^{-5}$ M), and either vehicle or flavonol ($10^{-4}$-$10^{-5}$ M) for 15 min before cumulative doses of phenylephrine ($10^{-9}$-$10^{-4.5}$ M) were added to generate a concentration-response curve to phenylephrine. Contraction responses were expressed as a percentage of KPSS-induced tension.

Vasorelaxation

Aortic rings were precontracted submaximally with phenylephrine ($10^{-8}$-$10^{-7}$ M) and the thromboxane mimetic, 9,11-dideoxy-9α,11α-epoxymethano-prostaglandin F2α (U46619, $10^{-10}$-$10^{-9}$ M) to approximately 50% of KPSS-induced contraction. After stabilization of the contraction, cumulative doses of the flavonol or vehicle ($10^{-10}$-$10^{-4}$ M) were added to generate a concentration-response curve. Relaxant responses were expressed as a percentage of the precontraction tension.

Effect of Flavonols on Superoxide Concentrations

Superoxide concentrations were measured in isolated aortic rings by lucigenin-enhanced chemiluminescence. Prior to assaying, the aortic rings were incubated at 37° C. for 1 h in Krebs-EPES buffer containing DETCA ($3\times10^{-5}$ M), which inactivates superoxide dismutase, NADPH ($10^{-4}$ M) and either vehicle, succinamic acid-substituted flavonol ($10^{-4}$ or $10^{-5}$ M) or diOHF ($10^{-4}$ or $10^{-5}$ M). Assay solutions consisting of lucigenin ($5\times10^{-6}$ M), NADPH ($10^{-4}$ M) and either vehicle (DMSO), succinamic acid-substituted flavonol ($10^{-4}$ or $10^{-5}$ M) or 3',4'-dihydroxyflavonol (diOHF, $10^{-4}$ or $10^{-5}$ M), as a positive control, were prepared in Krebs-HEPES buffer [composition (mM): NaCl, 99.0; KCl, 4.7; $KH_2PO_4$, 1.0; $MgSO_4.7H_2O$, 1.2; glucose, 11.0; $NaHCO_3$, 25.0; $CaCl_2.2H_2O$, 2.5; Na-HEPES, 20.0]. 300 µL aliquots of the assay solution were placed into separate wells on a 96-well Optiplate, which was loaded into a TopCount single photon counter (Packard Bioscience) to determine the background emission (12 cycles). After background counting was completed, one aortic ring was added per well, and photon emission was counted (12 cycles). Superoxide levels were reported as a percentage of photon emission for +NADPH control. At the conclusion of the assay, the aortic rings were dried for 48 h at 80° C. for normalization of superoxide production to dry tissue weight.

Data Presentation and Statistical Analysis

The results are expressed as the mean±s.e. mean and n indicates the number of experiments (rats). Relaxation concentration-response curves for diOHF were computer fitted to a sigmoidal curve using non-linear regression (Prism version 4) to enable calculation of $pEC_{50}$ of the flavonols. However, as in most cases the data did not fit a sigmoidal curve, $pEC_{50}$ was not calculated. Maximum relaxation responses were compared using a one way analysis of variance (ANOVA) with post-hoc multiple comparison using Newman-Keuls test. Superoxide levels were compared using a one way analysis of variance (ANOVA) with post hoc multiple comparison using Dunnett's test.

Finally, it is to be understood that various alterations, modifications and/or additions may be introduced into the constructions and arrangements of parts previously described without departing from the spirit or ambit of the invention.

What is claimed is:

1. A compound of the formula (I):

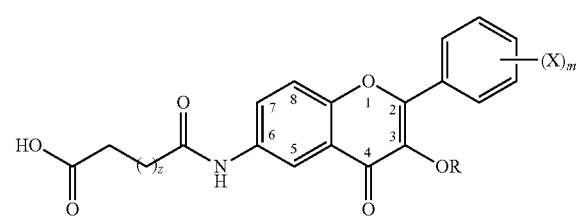

wherein

R is H;

X is OH;

m is an integer selected from the group consisting of 0, 1, 2, 3, 4 and 5;

z is an integer selected from 0, 1, 2 and 3;

or a pharmaceutically acceptable salt or prodrug thereof.

2. A compound according to claim 1 wherein m is selected from the group consisting of 0, 1 and 2.

3. A compound selected from the group consisting of:

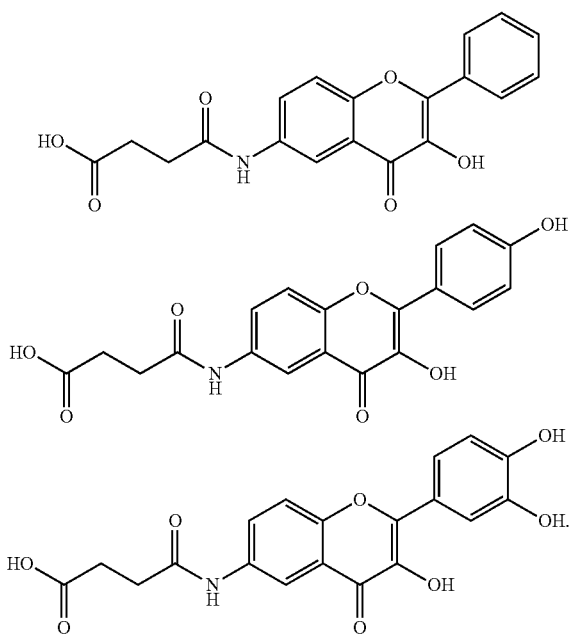

4. A method of achieving an anti-oxidant effect in a subject without eliciting a vasodilatory effect in the subject the method including administering an effective amount of a compound of formula (I) to the subject:

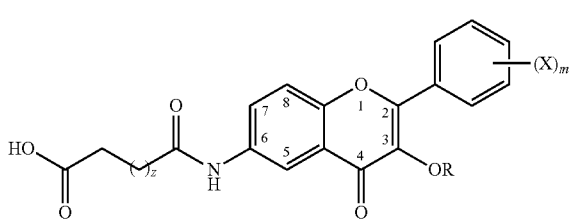

wherein
R is H;
X is OH;
m is an integer selected from the group consisting of 0, 1, 2, 3, 4 and 5;
z is an integer selected from 0, 1, 2 and 3;
or a pharmaceutically acceptable salt or prodrug thereof.

5. A method according to claim 4 wherein m is selected from the group consisting of 0, 1 and 2.

6. A method according to claim 4 wherein the compound is selected from the group consisting of:

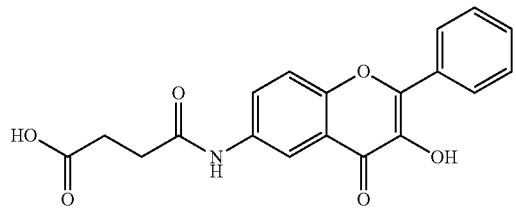

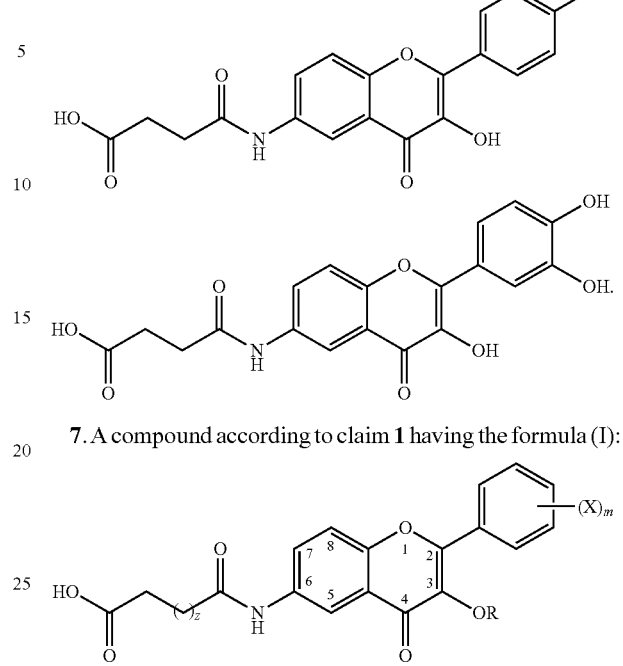

7. A compound according to claim 1 having the formula (I):

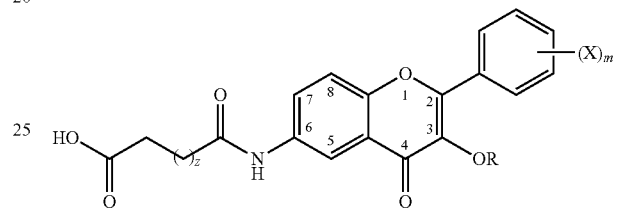

wherein R, X and m are as defined in claim 1.

8. A compound according to claim 1 having the formula (I):

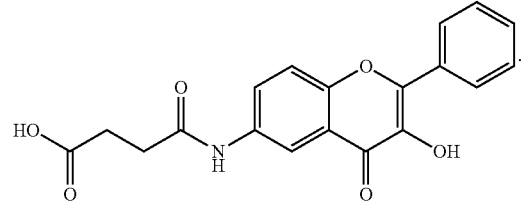

9. A compound according to claim 1 having the formula (I):

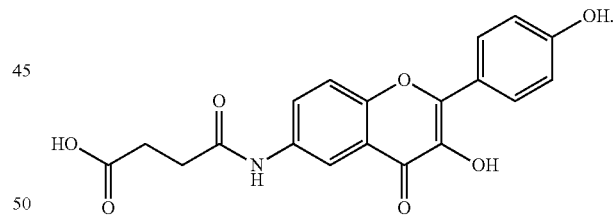

10. A compound according to claim 1 having the formula (I):

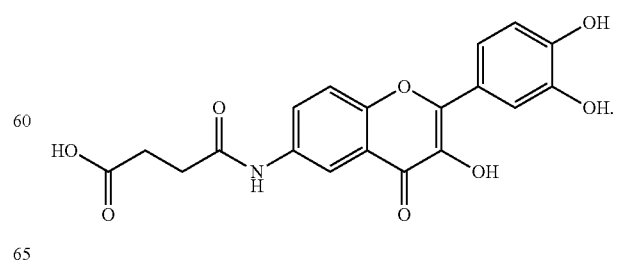

* * * * *

UNITED STATES PATENT AND TRADEMARK OFFICE
CERTIFICATE OF CORRECTION

PATENT NO. : 7,863,323 B1
APPLICATION NO. : 11/588795
DATED : January 4, 2011
INVENTOR(S) : Spencer J. Williams et al.

Page 1 of 1

It is certified that error appears in the above-identified patent and that said Letters Patent is hereby corrected as shown below:

Column 19, line 45, in Scheme 5: Delete " $\overset{a}{\rightarrow}$ " and replace with -- $\overset{b}{\rightarrow}$ --

Column 20, line 2: After "compound" delete "I," and replace with -- 1, --

Column 28, line 14: After "CDCl$_3$)" delete "d" and replace with -- δ --

Column 28, line 52: After "further" insert -- 50 --

Column 29, line 4: Delete "046619" and replace with -- U46619 --

In the Claims:
Column 32, line 25, Claim 7: Delete "( )$_z$" from the compound

Signed and Sealed this
Fifth Day of April, 2011

David J. Kappos
*Director of the United States Patent and Trademark Office*